(12) United States Patent
Doyle

(10) Patent No.: US 8,992,777 B2
(45) Date of Patent: Mar. 31, 2015

(54) SYSTEMS AND METHODS FOR PROVIDING NOTIFICATIONS IN DIALYSIS SYSTEMS

(75) Inventor: Matthew J. Doyle, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 657 days.

(21) Appl. No.: 13/299,790

(22) Filed: Nov. 18, 2011

(65) Prior Publication Data

US 2013/0132977 A1    May 23, 2013

(51) Int. Cl.
*B01D 61/32* (2006.01)
*A61M 1/16* (2006.01)
*G06F 7/50* (2006.01)
*G06F 9/50* (2006.01)
*G06F 19/00* (2011.01)

(52) U.S. Cl.
CPC ............ *G06F 19/3406* (2013.01); *B01D 61/32* (2013.01); *G06F 7/50* (2013.01); *G06F 9/50* (2013.01); *A61M 1/1601* (2014.02); *G06F 19/3481* (2013.01)
USPC ........................................................ 210/646

(58) Field of Classification Search
CPC .......... B01D 61/30; B01D 61/32; G06F 9/54; G06F 9/542; G06F 9/546; G06F 19/30; G06F 19/3406; G06F 19/348; G06F 7/50; G06F 9/50; G06F 19/3412; A61M 1/14; A61M 1/1601
USPC ............... 210/646, 739; 604/4.01, 5.01, 6.01, 604/6.09; 600/300, 301; 705/2, 3; 719/318; 708/490, 494, 670
See application file for complete search history.

(56) References Cited

U.S. PATENT DOCUMENTS

| 3,871,913 A | 3/1975 | Shaldon |
| 4,174,231 A | 11/1979 | Hobgood |
| 4,191,351 A | 3/1980 | Goyne |

(Continued)

FOREIGN PATENT DOCUMENTS

| EP | 0278100 | 8/1988 |
| EP | 0673658 | 9/1995 |

(Continued)

OTHER PUBLICATIONS

"RX Guide to Custom Dialysis," COBE Renal Care Inc., Revision E. Sep. 1993.

(Continued)

*Primary Examiner* — Joseph Drodge
(74) *Attorney, Agent, or Firm* — Onello & Mello, LLP

(57) ABSTRACT

A system and method provide information in response to at least one current event related to a treatment performed by a dialysis system. A first number is displayed at a treatment display in communication with the dialysis system. The first number corresponds to a set of current notifications. Each current notification is generated in response to at least one current event related to the treatment. A new event is detected that is related to the treatment. The first number is increased to a second number in response to detecting the new event. The second number corresponds to a new notification generated in response to the new event and corresponds to the set of current notifications. A highest priority event is determined between the new event and the at least one current event. The treatment display displays at least one notification corresponding to the highest priority event.

44 Claims, 16 Drawing Sheets

(56) References Cited

U.S. PATENT DOCUMENTS

| | | | |
|---|---|---|---|
| 4,581,141 A | 4/1986 | Ash | |
| 4,661,246 A | 4/1987 | Ash | |
| 4,666,598 A | 5/1987 | Heath et al. | |
| 4,684,460 A | 8/1987 | Issautier | |
| 4,728,496 A | 3/1988 | Petersen et al. | |
| 4,770,787 A | 9/1988 | Heath et al. | |
| 4,784,495 A | 11/1988 | Jonsson et al. | |
| 4,789,467 A | 12/1988 | Lindsay et al. | |
| 4,997,577 A | 3/1991 | Stewart | |
| 5,256,371 A | 10/1993 | Pippert | |
| 5,262,068 A | 11/1993 | Bowers et al. | |
| 5,277,820 A | 1/1994 | Ash | |
| 5,304,349 A | 4/1994 | Polaschegg | |
| 5,409,612 A | 4/1995 | Maltais et al. | |
| 5,421,813 A | 6/1995 | Ohnishi | |
| 5,473,536 A | 12/1995 | Wimmer | |
| 5,536,412 A | 7/1996 | Ash | |
| 5,589,070 A | 12/1996 | Maltais et al. | |
| 5,591,344 A | 1/1997 | Kenley et al. | |
| 5,603,902 A | 2/1997 | Maltais et al. | |
| 5,605,630 A | 2/1997 | Shibata | |
| 5,620,608 A | 4/1997 | Rosa et al. | |
| 5,643,212 A | 7/1997 | Coutre et al. | |
| 5,713,125 A | 2/1998 | Watanabe et al. | |
| 5,788,099 A | 8/1998 | Treu et al. | |
| 5,919,369 A | 7/1999 | Ash | |
| 5,944,684 A | 8/1999 | Roberts et al. | |
| 6,000,567 A | 12/1999 | Carlsson et al. | |
| 6,036,858 A | 3/2000 | Carlsson et al. | |
| 6,086,753 A | 7/2000 | Ericson et al. | |
| 6,143,181 A | 11/2000 | Falkvall et al. | |
| 6,170,785 B1 | 1/2001 | Lampropoulos et al. | |
| 6,188,407 B1 | 2/2001 | Smith et al. | |
| 6,190,855 B1 | 2/2001 | Herman et al. | |
| 6,277,277 B1 | 8/2001 | Jacobi et al. | |
| 6,280,632 B1 | 8/2001 | Polaschegg | |
| 6,308,721 B1 | 10/2001 | Bock et al. | |
| 6,409,699 B1 | 6/2002 | Ash | |
| 6,411,836 B1 | 6/2002 | Patel et al. | |
| 6,416,293 B1 | 7/2002 | Bouchard et al. | |
| 6,428,706 B1 | 8/2002 | Rosenqvist et al. | |
| 6,627,164 B1 | 9/2003 | Wong | |
| 6,755,976 B2 | 6/2004 | Rosenqvist et al. | |
| 6,818,196 B2 | 11/2004 | Wong | |
| 6,878,283 B2 | 4/2005 | Thompson | |
| 7,033,498 B2 | 4/2006 | Wong | |
| 7,077,956 B2 | 7/2006 | Rovatti | |
| 7,101,519 B2 | 9/2006 | Wong | |
| 7,169,303 B2 | 1/2007 | Sullivan et al. | |
| 7,241,272 B2 | 7/2007 | Karoor et al. | |
| 7,273,465 B2 | 9/2007 | Ash | |
| 7,410,475 B2 * | 8/2008 | Krensky et al. | 604/29 |
| 7,566,432 B2 | 7/2009 | Wong | |
| 7,756,722 B2 * | 7/2010 | Levine et al. | 705/2 |
| 7,867,214 B2 | 1/2011 | Childers et al. | |
| 7,899,683 B2 | 3/2011 | Schoenberg et al. | |
| 7,904,824 B2 | 3/2011 | Stern et al. | |
| 8,029,454 B2 | 10/2011 | Kelly et al. | |
| 8,376,943 B2 * | 2/2013 | Kovach et al. | 600/300 |
| 8,403,881 B2 * | 3/2013 | Ferren et al. | 604/65 |
| 2002/0001794 A1 | 1/2002 | Melker et al. | |
| 2002/0079695 A1 | 6/2002 | Campbell et al. | |
| 2002/0138512 A1 | 9/2002 | Buresh et al. | |
| 2004/0019312 A1 | 1/2004 | Childers et al. | |
| 2004/0022717 A1 | 2/2004 | Wong | |
| 2004/0050789 A1 | 3/2004 | Ash | |
| 2004/0070201 A1 | 4/2004 | Niermeyer et al. | |
| 2005/0031523 A1 | 2/2005 | Wong | |
| 2005/0131332 A1 | 6/2005 | Kelly et al. | |
| 2005/0274658 A1 | 12/2005 | Rosenbaum et al. | |
| 2007/0158247 A1 | 7/2007 | Carr et al. | |
| 2007/0158249 A1 | 7/2007 | Ash | |
| 2007/0158268 A1 | 7/2007 | DeComo | |
| 2007/0161113 A1 | 7/2007 | Ash | |
| 2007/0161941 A1 | 7/2007 | Ash et al. | |
| 2007/0179431 A1 | 8/2007 | Roberts et al. | |
| 2007/0181499 A1 | 8/2007 | Roberts et al. | |
| 2008/0149563 A1 | 6/2008 | Ash | |
| 2008/0177216 A1 | 7/2008 | Ash | |
| 2009/0037216 A1 | 2/2009 | Bluemler et al. | |
| 2009/0061404 A1 | 3/2009 | Toly | |
| 2009/0127193 A1 | 5/2009 | Updyke et al. | |
| 2009/0222119 A1 | 9/2009 | Plahey et al. | |
| 2009/0309835 A1 * | 12/2009 | Levin et al. | 345/168 |
| 2010/0131883 A1 | 5/2010 | Linthicum et al. | |
| 2011/0000832 A1 | 1/2011 | Kelly et al. | |
| 2011/0004351 A1 | 1/2011 | Kelly et al. | |
| 2011/0005986 A1 | 1/2011 | Kelly et al. | |
| 2011/0005992 A1 | 1/2011 | Kelly et al. | |
| 2011/0009797 A1 | 1/2011 | Kelly et al. | |
| 2011/0009798 A1 | 1/2011 | Kelly et al. | |
| 2011/0017665 A1 | 1/2011 | Updyke et al. | |
| 2011/0022239 A1 * | 1/2011 | Forbes et al. | 700/286 |
| 2011/0077470 A1 | 3/2011 | Hussain et al. | |
| 2011/0105983 A1 | 5/2011 | Kelly et al. | |
| 2011/0141116 A1 * | 6/2011 | Dalesch et al. | 345/440 |
| 2011/0160637 A1 | 6/2011 | Beiriger | |
| 2011/0204092 A1 | 8/2011 | Niermeyer et al. | |
| 2011/0297593 A1 | 12/2011 | Kelly et al. | |
| 2011/0303588 A1 | 12/2011 | Kelly et al. | |
| 2012/0018378 A1 | 1/2012 | Kelly et al. | |
| 2012/0022441 A1 | 1/2012 | Kelly et al. | |
| 2012/0043279 A1 | 2/2012 | Kelly et al. | |
| 2012/0085707 A1 | 4/2012 | Beiriger | |
| 2012/0138533 A1 | 6/2012 | Curtis et al. | |
| 2012/0154264 A1 * | 6/2012 | Wang et al. | 345/156 |
| 2013/0158932 A1 * | 6/2013 | Witter et al. | 702/108 |
| 2013/0165847 A1 * | 6/2013 | Scarpaci et al. | 604/28 |
| 2014/0180711 A1 * | 6/2014 | Kamen et al. | 705/2 |

FOREIGN PATENT DOCUMENTS

| | | | |
|---|---|---|---|
| EP | 1096991 | | 5/2001 |
| EP | 1170659 | A2 | 1/2002 |
| EP | 1342480 | | 9/2003 |
| EP | 1426912 | | 6/2004 |
| EP | 2087916 | | 8/2009 |
| GB | 2124511 | | 2/1984 |
| WO | 9702055 | | 1/1997 |
| WO | 9702056 | | 1/1997 |
| WO | 9817333 | | 4/1998 |
| WO | 9841267 | A1 | 9/1998 |
| WO | 9937342 | | 7/1999 |
| WO | 0002650 | | 1/2000 |
| WO | 0230267 | | 4/2002 |
| WO | 0243859 | | 6/2002 |
| WO | 2004009158 | | 1/2004 |
| WO | 2004105589 | | 12/2004 |
| WO | 2005044339 | | 5/2005 |
| WO | 2005123230 | | 12/2005 |
| WO | 2007028056 | | 3/2007 |
| WO | 2007081383 | | 7/2007 |
| WO | 2007081384 | | 7/2007 |
| WO | 2007081565 | | 7/2007 |
| WO | 2007081576 | | 7/2007 |

OTHER PUBLICATIONS

"Sorbent Dialysis Primer," COBE Renal Care, Inc., Sep. 4, 1993 Ed. 4.

Blumenkrantz, et al., "Applications of the Redy Sorbent System to Hemodialysis and Peritoneal Dialysis;" Artificial Organs, 3(3):230-236, 1978.

Operator's Manual—Fresenius 2008K Hemodialysis Machine (2000).

Hans-Dietrich Polaschegg, "Neglected Safety Aspects in Hemodialysis Machines and Their Related Problems;" Hemodialysis Horizons, pp. 65-68.

Madhukar Misra, "The basics of hemodialysis equipment;" Hemodialysis International 2005; 9: pp. 30-36.

"Systems and Method for Displaying Objects at a Medical Treatment Apparatus Display Screen" Specification, Drawings, Claims and

(56) References Cited

OTHER PUBLICATIONS

Prosecution History, of U.S. Appl. No. 13/365,714, filed Feb. 2, 2012, by Matthew J. Doyle, et al.
"Systems and Methods for Compensation of Compliant Behavior in Regenerative Dialysis Systems" Specification, Drawings, Claims and Prosecution History, of U.S. Appl. No. 12/902,702, filed Oct. 12, 2010, by Matthew J. Doyle.

PCT International Search Report and Written Opinion dated Apr. 15, 2014 issued in corresponding PCT Application No. US 2013/076967.
International Search Report and Written Opinion issued on May 14, 2013 in related International Application No. PCT/US2012/065248.
International Search Report and Written Opinion issued on Jul. 9, 2013 in related International Application No. PCT/US2013/024361.

* cited by examiner

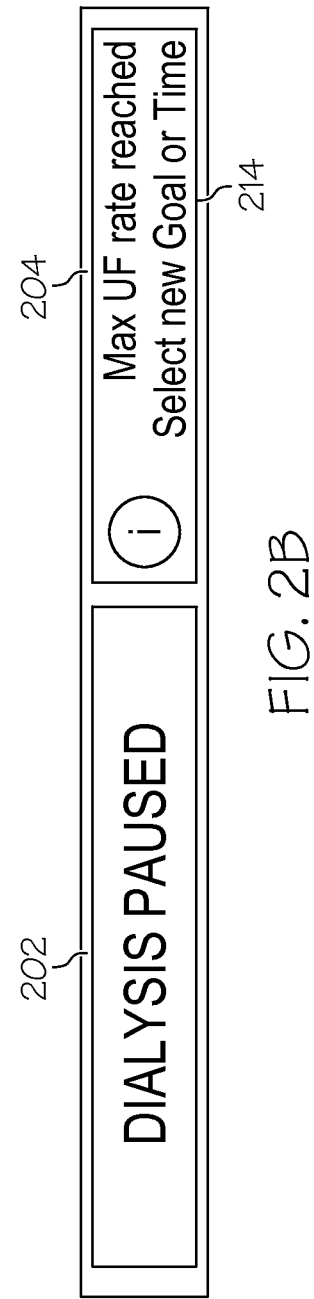
FIG. 2A
FIG. 2B

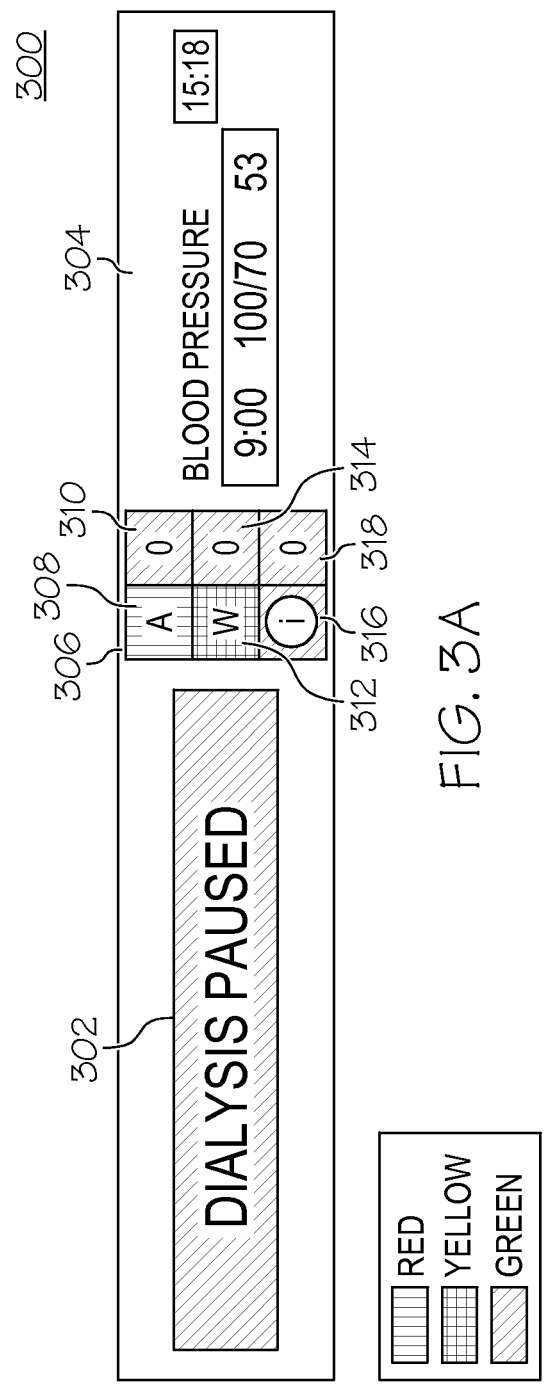

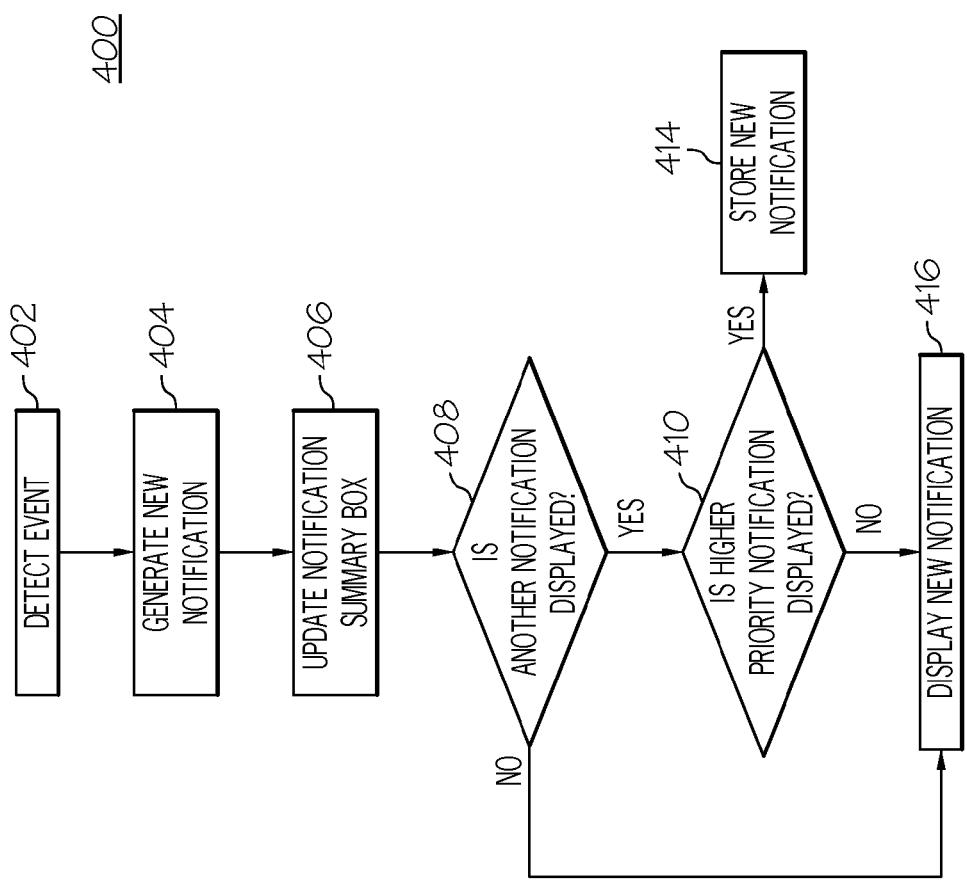

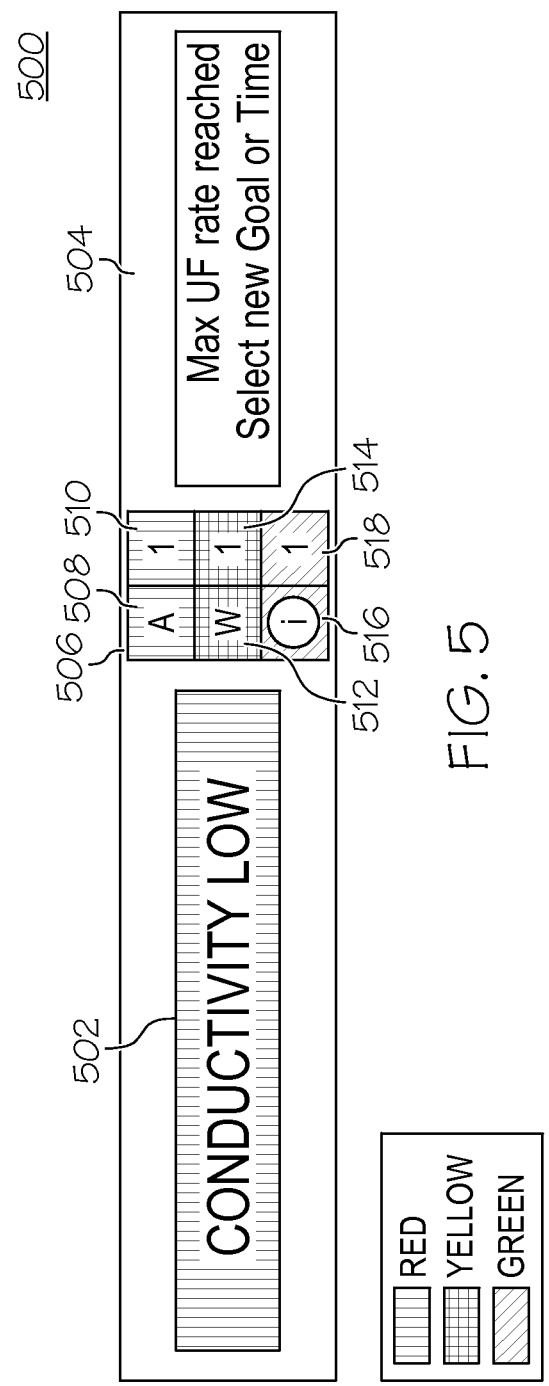

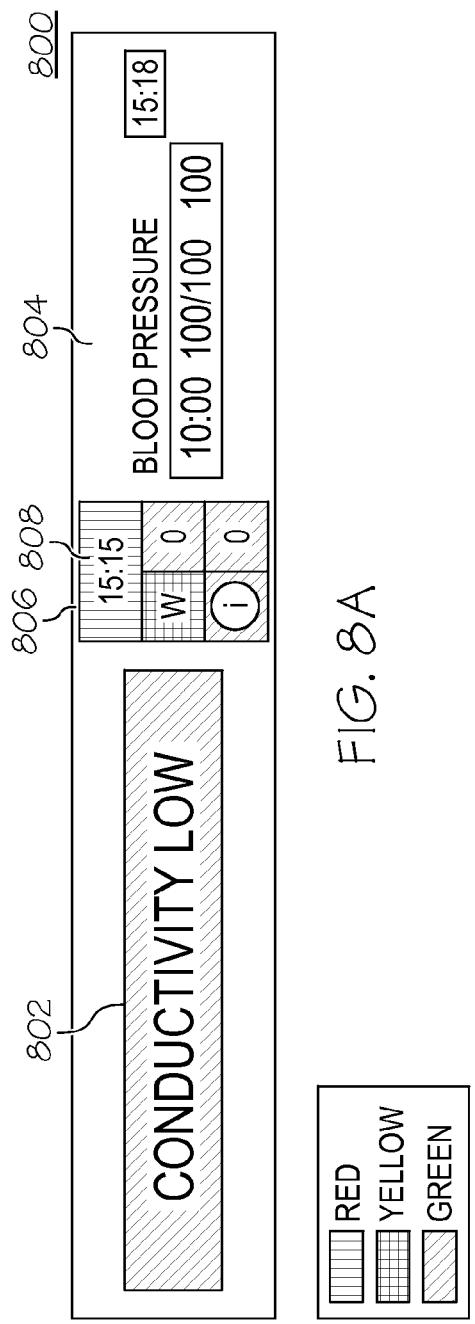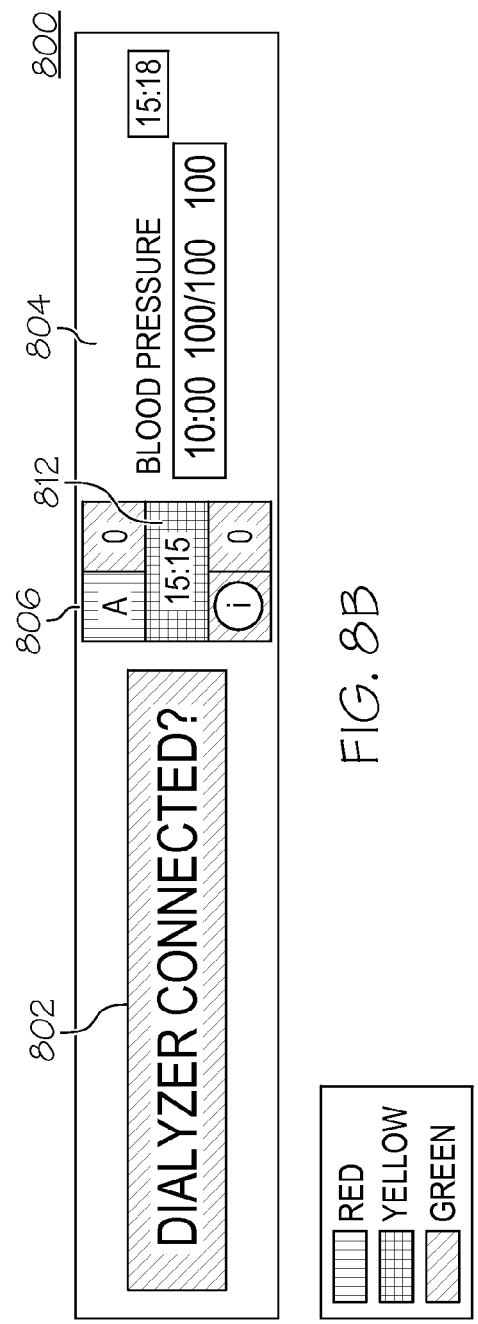

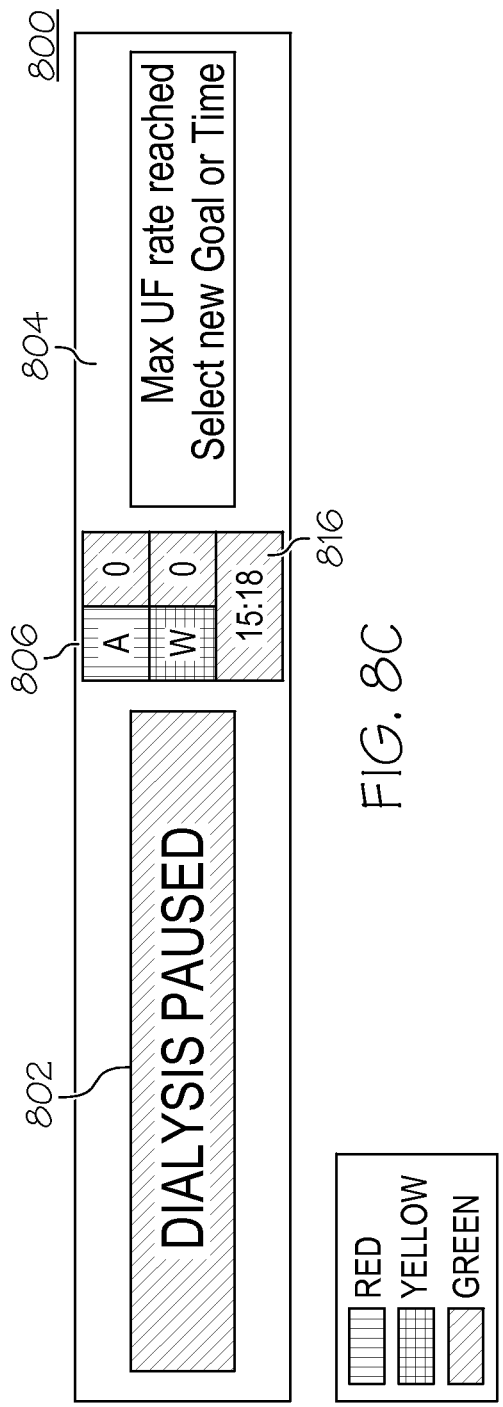

SYSTEMS AND METHODS FOR PROVIDING NOTIFICATIONS IN DIALYSIS SYSTEMS

BACKGROUND

Hemodialysis machines are commonly used to treat medical conditions related to renal failure, where a person's kidneys inadequately filter toxins and waste products from the blood. During a hemodialysis procedure, blood is removed from the patient and output to a dialyzer. The patient's blood circulates along one side of a semipermeable membrane in the dialyzer, and a dialysate flows along the opposite side of the membrane to remove waste, toxins, and other undesirable products from the blood. In a regenerative dialysis system, the used dialysate is pumped through a sorbent cartridge, which purifies the dialysate by removing the waste so that a constant stream of fresh dialysate is provided to the dialyzer. In a non-regenerative dialysis system, the used dialysate is discarded.

It is important that hemodialysis machines and other regenerative dialysis systems provide a comprehensive monitoring system that detects abnormal events that may pose a threat to patient safety during a dialysis procedure and that generates clear and unambiguous notifications when such events occur.

BRIEF SUMMARY

In one aspect, a computer-implemented method is provided for displaying information in response to at least one event related to a treatment performed by a dialysis system. The method comprises displaying a first number at a treatment display, the first number corresponding to a set of current notifications generated in response to at least one current event related to the treatment; detecting a new event related to the treatment; increasing the first number to a second number in response to detecting the new event, the second number corresponding to a combination of a new notification generated in response to the new event and the set of current notifications; determining a highest priority event between the new event and the at least one current event; and displaying at the treatment display at least one notification corresponding to the highest priority event.

In an embodiment, the computer-implemented method further comprises configuring the treatment display to include a status box, a dialog box, and a notification summary box; displaying at least one of the first number and the second number at the notification summary box; and displaying the at least one notification corresponding to the highest priority event at the status box or the dialog box.

In an embodiment, the at least one of the first number and the second number is displayed at a first region of the notification summary box corresponding to a set of alarm notifications, or is displayed at a second region of the notification summary box corresponding to a set of advisory notifications, or is displayed at a third region of the notification summary box corresponding to a set of dialog messages.

In an embodiment, the set of advisory notifications include at least one of a warning message and a status advisory message.

In an embodiment, the computer-implemented method further comprises displaying an alarm notification, a warning notification, or a status advisory notification of the set of alarm notifications and the advisory notifications, respectively, at the status box of the treatment display.

In an embodiment, the computer-implemented method further comprises displaying a dialog message of the set of dialog messages at the dialog box of the treatment display.

In an embodiment, the computer-implemented method further comprises displaying at the notification summary box a time of occurrence of the highest priority event.

In an embodiment, the computer-implemented method further comprises cycling between the at least one notification corresponding to the highest priority event and the current notifications corresponding to lower priority events; and displaying at the treatment display a current notification of the set of current notifications during the cycling.

In an embodiment, the computer-implemented method further comprises displaying a help screen at the treatment display corresponding to the displayed current notification of the set of current notifications or the displayed at least one notification corresponding to the highest priority event.

In an embodiment, the computer-implemented method further comprises displaying at the notification summary box a time of occurrence of an event of the at least one current event from which the displayed current notification of the set of current notifications is generated.

In an embodiment, the computer-implemented method further comprises storing the set of current notifications and the at least one notification corresponding to the highest priority event at a storage device; and retrieving the stored current notification of the current notifications for display during the cycling between the at least one notification corresponding to the highest priority event and the current notifications.

In an embodiment, the highest priority event complies with a color code, each color in the color code referring to a severity of the event, and wherein the current notification is displayed during the cycling at a region of the treatment display that displays a color of the color code corresponding to the highest priority event.

In an embodiment, the computer-implemented method further comprises displaying a first notification corresponding to the highest priority event; selecting for display a second notification corresponding to a lower priority event between the new event and the at least one current event; configuring a timer to display the second notification for a predefined period of time; displaying the second notification during the predefined period of time; and automatically displaying the first notification following the predefined period of time.

In an embodiment, the first number is zero, and wherein a default status advisory message is displayed at the treatment display.

In an embodiment, the computer-implemented method further comprises determining a highest priority event includes determining a highest priority between different alarms, warnings, status advisory messages, dialog messages, or a combination thereof.

In an embodiment, the at least one current event is an incorrectly entered parameter for configuring the dialysis system or an event capable of endangering a patient during a dialysis procedure.

In another aspect, a computer-implemented method is provided for displaying information in response to at least one event related to a treatment performed by a dialysis system. The method comprises displaying, at a treatment display, an indicator indicating that two or more notifications are available for display in response to the at least one event; and displaying, at the treatment display, at least one notification of the two or more notifications.

In an embodiment, the computer-implemented method further comprises selecting another notification of the two or more notifications from the treatment display; and displaying the other notification in response to the selection.

In an embodiment, the indicator comprises a number corresponding to the two or more notifications available for display.

In an embodiment, the computer-implemented method further comprises generating a new notification; and adjusting the number of notifications to include a combination of the new notification and the two or more notifications available for display.

In an embodiment, the computer-implemented method further comprises removing a notification from the number of notifications available for display; and decrementing the number of notifications to include a reduced number of notifications available for display.

In an embodiment, the two or more notifications are categorized into an alarm notification category, an advisory message notification category, and a dialog message category.

In an embodiment, the advisory message notification category includes at least one of a warning message notification category and a status advisory message notification category.

In an embodiment, the computer-implemented method further comprises displaying at the treatment display a highest priority notification of a highest priority category selected from the alarm notification category, the advisory message notification category, and the dialog message category.

In an embodiment, the alarm notification category is selected as the highest priority category.

In an embodiment, the computer-implemented method further comprises determining a highest priority notification between different alarms, warnings, status advisory messages, dialog messages, or a combination thereof; and displaying at the treatment display the determined highest priority notification.

In another aspect, a notification system for a dialysis system comprises an event signal detector, a notification generator, and a notification summary generator. The event signal detector receives event signals generated in response to detected events related to a treatment performed by the dialysis system. The notification generator processes the event signals to generate a set of notifications. The notification summary generator generates a number corresponding to the set of notifications and outputs the number to a treatment display.

In an embodiment, the notification summary generator generates a first number corresponding to zero or more current notifications of the set of notifications, and generates a second number in response to a detected new event, the second number corresponding to a combination of a new notification generated from the new event and the set of current notifications.

In an embodiment, the notification summary generator forms a notification summary box that is displayed at the treatment display and that is populated with at least one of the first number and the second number.

In an embodiment, the notification summary generator provides the at least one of the first number and the second number at a first region of the notification summary box corresponding to a set of alarm notifications, or at a second region of the notification summary box corresponding to a set of advisory notifications, or at a third region of the notification summary box corresponding to a set of dialog messages.

In an embodiment, the notification generator outputs to the notification summary box a time of occurrence of an event to which a currently displayed notification corresponds.

In an embodiment, the set of advisory notifications includes at least one of a warning message and a status advisory message.

In an embodiment, the notification system further comprises a notification priority module that determines a priority of each event of the plurality of events.

In an embodiment, the notification generator outputs a notification to the treatment display that corresponds to a highest priority event of the plurality of events.

In an embodiment, the notification system further comprises a timer that establishes a period of time during which a different notification than the notification corresponding to the highest priority event is displayed at the treatment display, and the timer automatically displays the notification corresponding to the highest priority event at the treatment display at the end of the period of time.

In an embodiment, the notification priority module determines a highest priority between different alarms, warnings, status advisory messages, dialog messages, or a combination thereof.

In an embodiment, the notification system further comprises a notification cycling module and a data repository, the data repository storing the set of notifications, the notification cycling module retrieving a notification of the stored set of notifications for display during a cycling between the set of notifications.

In an embodiment, the notification cycling module retrieves help screen data corresponding to the set of notifications from the data repository and outputs the help screen data to the treatment display.

In another aspect, a computer-implemented method is provided for determining a notification for display, the notification corresponding to an event related to a treatment performed by a dialysis system. The method comprises generating at least two notifications, each notification generated in response to an event related to the treatment; displaying at least one number corresponding to the at least two notifications at a first region of a treatment display; displaying a first highest priority notification of the at least two notifications at a second region of the treatment display; and cycling between the first highest priority notification and other notifications of the at least two notifications to display at least one other notification of the other notifications at the treatment display.

In an embodiment, cycling between the first highest priority notification and other notifications includes cycling between at least two alarms, warnings, status advisory messages, or a combination thereof; and displaying the at least two alarms, warnings, status advisory messages or a combination thereof, one at a time, at a status box of the treatment display.

In an embodiment, the computer-implemented method further comprises cycling between the at least two alarms; and automatically activating a warning field at the first region of the treatment display to display one or more warnings, status advisory messages, or a combination thereof, at the status box.

In an embodiment, the computer-implemented method further comprises cycling between at least two warnings, status advisory messages, or a combination thereof, at the status box.

In an embodiment, the computer-implemented method further comprises cycling between the at least two alarms; and manually selecting a warning field at the first region of the treatment display to display one or more warnings, status advisory messages, or a combination thereof, at the status box.

In an embodiment, the computer-implemented method further comprises cycling between at least two warnings, status advisory messages, or a combination thereof, at the status box.

In an embodiment, cycling between the first highest priority notification and other notifications includes cycling between at least two dialog messages; and displaying the at least two dialog messages, one at a time, at a dialog box of the treatment display.

In an embodiment, displaying the at least one number comprises displaying a first number at the treatment display, the first number corresponding to the at least two notifications; detecting a new event related to the treatment; replacing the first number with a second number in response to detecting the new event, the second number corresponding to a combination of a new notification generated in response to the new event and the at least two notifications; determining a second highest priority notification between the new notification and the first highest priority notification; and displaying at the treatment display the second highest priority notification.

In an embodiment, the computer-implemented method further comprises providing a notification summary box at the first region of the treatment display, wherein the at least one of the first number and the second number is displayed at a first section of the notification summary box corresponding to a set of alarm notifications, or is displayed at a second section of the notification summary box corresponding to a set of advisory notifications, or is displayed at a third section of the notification summary box corresponding to a set of dialog messages.

In an embodiment, the notification generator outputs to the notification summary box a time of occurrence of an event to which a currently displayed notification corresponds.

In an embodiment, the set of advisory notifications include at least one of a warning message and a status advisory message.

In an embodiment, the computer-implemented method further comprises displaying a help screen at the treatment display corresponding to the displayed first highest priority notification.

In an embodiment, the computer-implemented method further comprises displaying a help screen at the treatment display corresponding to the at least one other notification.

In an embodiment, displaying at least one other notification of the other notifications at the treatment display includes displaying each of the at least two notifications in an order of a predetermined priority of each notification.

In an embodiment, the first highest priority event complies with a color code, each color in the color code referring to a severity of the event, and wherein the other notification is displayed during the cycling at a region of the treatment display that displays a color of the color code corresponding to the first highest priority event.

In an embodiment, a computer program product is provided for displaying information in response to at least one current event related to a treatment performed by a dialysis system. The computer program product comprises a computer readable storage medium having computer readable program code embodied therewith. The computer readable program code comprises: computer readable program code configured to display a first number at a treatment display, the first number corresponding to a set of current notifications generated in response to at least one current event related to the treatment; computer readable program code configured to detect a new event related to the treatment; computer readable program code configured to increment the first number to a second number in response to detecting the new event, the second number corresponding to a combination of a new notification generated in response to the new event and the set of current notifications; computer readable program code configured to determine a highest priority event between the new event and the at least one current event; and computer readable program code configured to display at the treatment display a notification corresponding to the highest priority event.

BRIEF DESCRIPTION OF THE SEVERAL VIEWS OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 2A is a screenshot of a status section of a conventional treatment display;

FIG. 2B is a screenshot of the status section of FIG. 2A displaying an informational message;

FIG. 3A is a screenshot of a status section of a treatment display having a notification summary box, in accordance with an embodiment;

FIG. 4 is a flowchart of a method for displaying a notification in response to a dialysis event, in accordance with an embodiment;

FIG. 5 is a screenshot of a status section of a treatment display presenting an alarm notification complying with the method of FIG. 4, in accordance with another embodiment;

FIGS. 8A-8C are screenshots of a status section of a treatment display presenting a time of occurrence of past and present alarms, in accordance with another embodiment;

DETAILED DESCRIPTION

Figure 1:
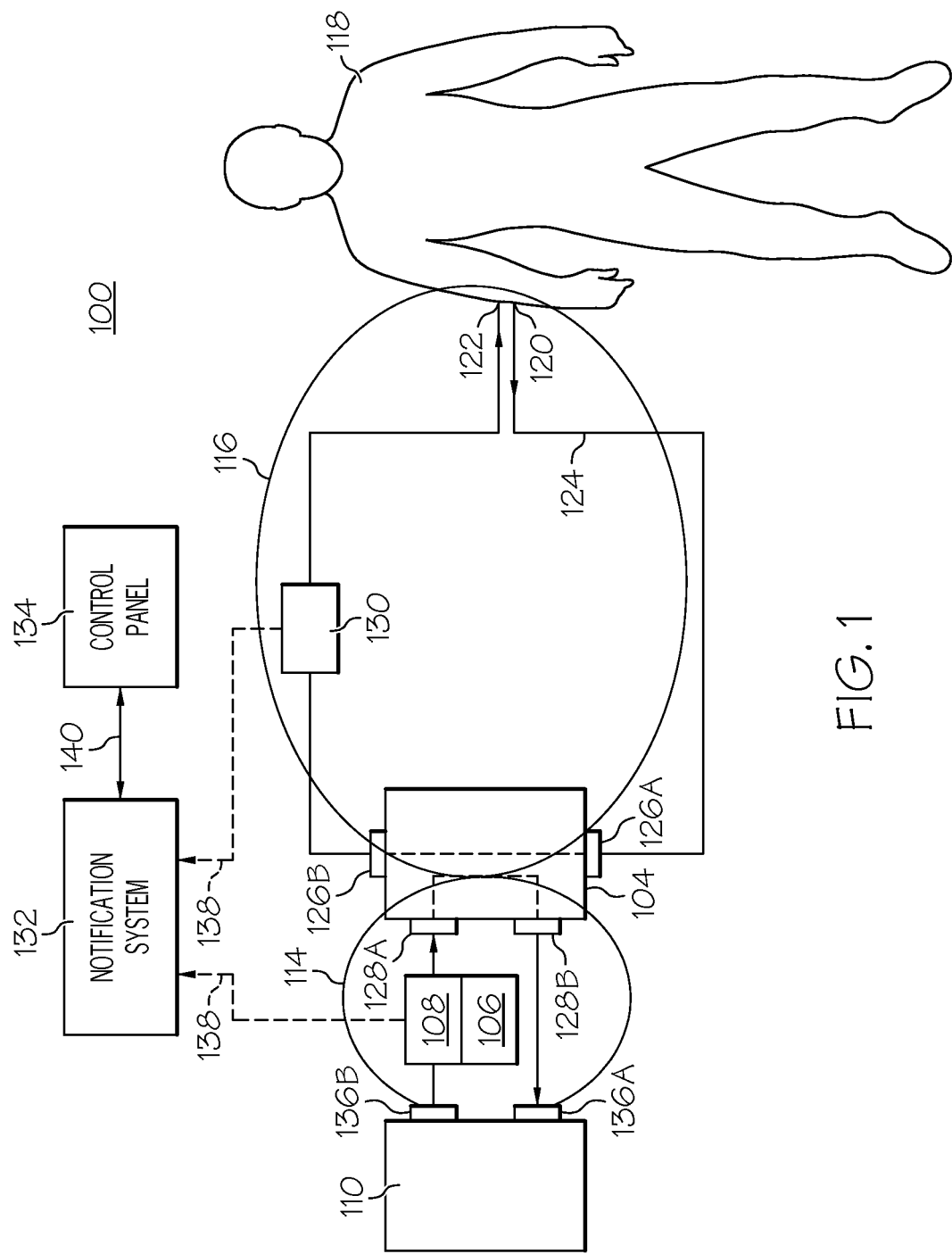
FIG. 1 is a schematic block diagram of a dialysis system, in which embodiments of the present inventive concepts can be practiced.

Embodiments will now be described more fully hereinafter with reference to the accompanying drawings, in which embodiments of the invention are shown. This invention may, however, be embodied in many different forms and should not be construed as limited to the embodiments set forth herein. Like numbers refer to like elements throughout.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. As used herein, the term "and/or" includes any and all combinations of one or more of the associated listed items and may be abbreviated as "/".

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent," etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Hemodialysis machines typically include event detection and monitoring systems that detect abnormal events occurring prior to or during a dialysis procedure. Such systems include a console having a monitor that displays an alarm, a warning, or an informational message generated in response to the detected event. A limitation of these systems is that one event-related message is displayed at a time. When multiple alarms or a combination of alarms and warnings are generated, the highest priority alarm is displayed, for example, an alarm corresponding to a life-threatening event. Help screens can be available to assist an operator with interpreting an alarm, or to suggest a course of action. However, when the operator selects a help button at the console, only the help screen corresponding to the highest priority alarm is displayed.

In brief overview, aspects of the present inventive concepts include a notification system for a regenerative dialysis system that provides a notification summary box, permitting an operator or other viewer to obtain a "snapshot" of the current status of the dialysis system, by viewing multiple alarms, warnings, status advisory messages, or other information before the highest priority alarm is cleared. In this manner, the operator or other viewer can obtain valuable information as to the cause of an alarm by viewing other event-related information, such as other alarms or warnings.

The notification summary box includes at least three buttons, in particular, an alarm summary button, a warning summary button, and a dialog message summary button. The notification summary box also includes a display field adjacent each button for displaying a number that corresponds to a set of outstanding notifications. A display field adjacent the alarm summary button displays a number corresponding to a set of outstanding alarms. A display field adjacent the warning summary button displays a number corresponding to a set of outstanding warnings and/or status advisory messages. A display field adjacent the dialog message summary button displays a number corresponding to a set of outstanding dialog messages. Each button when selected can provide additional information related to the corresponding outstanding notifications at another region of the display, for example, at a status box or a dialog box of the display. This information can include historical information, for example, regarding previously-generated alarms, a time of occurrence of previous events, help-related information, and the like. When a button is selected, or when a new event is detected, a predetermined priority scheme is activated that establishes which alarm, warning, or other related notification is to be displayed first. Priorities can be determined between two or more alarms, warnings, status advisory messages, and/or dialog messages.

Another feature is that, in some embodiments, a user can cycle between different notifications as well as between help screens corresponding to these notifications if more than one notification is generated. Thus, low priority notifications such as warnings can be displayed in addition to high priority alarms. Here, a timer can be activated, where a low priority notification is displayed for a predefined period of time, to ensure that the highest priority notification is redisplayed. If a new event occurs having a higher priority than an event corresponding to a currently displayed notification, then the timer ensures that the notification corresponding to the new event is displayed.

When new notifications are generated, the number of notifications displayed at the notification summary box is incremented. Also, the corresponding display field can flash or provide another indicator that a new notification has been generated. On the other hand, when current alarms, warnings, and the like, are addressed, the number of notifications can be decremented. If a new notification has a higher priority than a currently displayed notification, then the new notification is displayed. Otherwise, the new notification is stored, and can be retrieved when a user cycles between the current notifications on the display.

FIG. 1 is a schematic block diagram of a dialysis system 100, in which embodiments of the present inventive concepts can be practiced. In an embodiment, the dialysis system 100 includes a hemodialysis machine 104 or a related regenerative dialysis machine for performing hemodialysis or related procedures. While a regenerative dialysis system is depicted, embodiments of the present inventive concepts are equally applicable to non-regenerative dialysis systems, and other types of dialysis systems.

During a hemodialysis procedure, two needles 120, 122 are inserted into a region of a patient's body 118 for extracting blood from the body 118 and introducing cleaned blood to the body 118, respectively. Although a two-needle system is depicted and described, embodiments of the present inventive concepts are equally applicable to a single needle system.

An extracorporeal circuit (ECC) 116, also referred to as a dialysis circuit or blood circuit, is formed between the needles 120, 122, where blood flows out of the body 118 via the first needle 120 through a plastic tubing 124 and into a hemodialysis machine 104 via an input port 126A. The hemodialysis machine 104 includes a dialyzer or related filtration device that removes toxins, waste, and impurities such as urea, and/or excess fluid such as water from the blood, and outputs the cleaned blood via an output port 126B of the dialyzer to the body 118 via the second needle 122. During this procedure, the ECC 116 is monitored for venous and arterial blood pressures, and for the presence of air and blood, among other monitored parameters. This cycle can be repeated as necessary during the procedure.

Also during the procedure, a second circuit, referred to as a dialysate circuit 114, is formed between the hemodialysis machine 104 and a dialysate system 110. The dialysate system 110 outputs dialysate mixed with purified water from an output port 136B to the dialyzer of the hemodialysis machine 104 via an input port 128A, also referred to as a dialyzer connector. Here, at the dialyzer, toxins, waste, and the like are transferred from the circulating blood to the dialysate via diffusion or osmosis occurring across the membrane. The used dialysate containing the waste and the like is output from the hemodialysis machine 104 via an output port 128B to an input port 136A at the dialysate system 110 to a sorbent cartridge (not shown), which purifies the dialysate by removing the waste and the like from the used dialysate. The purified dialysate can then be output from the output port 136B of the dialysate system 110 to the hemodialysis machine 104 where the cycle can be repeated. The hemodialysis machine 104 and the dialysate system 110 can include other elements such as pumps, sensors, filters, and the like, which are well-known to those of ordinary skill in the art and will therefore not be described herein for reasons related to brevity.

The dialysis system 100, in addition to the dialysate system 110 and the hemodialysis machine 104, includes various monitors, meters, sensors, detectors, and the like along the ECC 116 and/or the dialysate circuit 114 to monitor an array of safety-critical parameters, including blood and dialysate flow rates, blood pressure, dialysis solution conductivity, temperature, pH, and other parameters. These parameters can be determined by monitors, sensors and the like prior to or during a dialysis procedure.

In one example, the dialysis system 100 can include a dialysate temperature sensor 108 along the dialysate path 114 that monitors the temperature of the dialysate. An abnormal change in the dialysate temperature can result in a corresponding change in the patient's body temperature, which can damage the blood and lead to serious injury or death. Accordingly, if the sensor 108 detects a high or low dialysate temperature reading, an event signal 138 can be generated to activate an alarm at the control panel 134 to alert a patient-care technician, clinician, and the like.

In another example, the dialysis system 100 can include a dialysate conductivity monitor 106 along the dialysate path 114. During operation, an operator can alter the proportioning of dialysate concentrate with inlet water by selecting a concentrate amount from the control panel. In this manner, an operator can change the inflowing dialysate conductivity in a predictable manner. The concentration delivered to the hemodialysis machine 104 is critical for the correct performance of the procedure and can usually be adjusted in a proportioning pump or other mixing device. If the sensor dialysate conductivity monitor 106 detects that an actual or measured conductivity has exceeded a predefined low conductivity alarm limit, then an event signal 138 can be generated to activate a dialysate alarm at the control panel 134 to alert a patient-care technician, clinician, and the like.

In yet another example, the dialysis system 100 can include a venous pressure monitor 130 along the ECC path 116, in this example, between the output port 126B of the dialyzer of the hemodialysis machine 104 and the patient 118 to sense a venous blood pressure, and to generate an event signal 138 used to activate an alarm when an abnormal venous blood pressure is detected, for example, when the venous blood pressure has exceeded a predefined alarm limit. The dialysis system 100 includes many other sensors, monitors, detectors, and the like, for example, an arterial pressure monitor, which are not described herein for reasons related to brevity.

The notification system 132 can receive an event signal 138 from the dialysate temperature sensor 108, the dialysate conductivity monitor 106, the pressure monitor 130, and/or from other detectors, sensors, and the like, indicating an event, for example, a low conductivity level. An event can also be generated at the control panel 134 when a user enters an incorrect parameter, which can trigger a dialog message displayed at the control panel 134. The notification system 132 generates a status summary from the received event signals 138, and outputs the status summary data via a data path 140 to the control panel 134. The notification system 132 can be directly connected to the control panel 134 by a data bus or related connector. Alternatively, the notification system 132 and the control panel 134 can communicate with each other via the data path 140 formed through a network, for example, a local network (LAN).

The control panel 134 includes a display screen and other input/output devices, such as a keypad, a touchpad, a keyboard, and/or a mouse. The display screen presents a treatment display, which permits an operator to provide treatment parameters related to a dialysis procedure and to monitor the dialysis system 100 for events related to a procedure.

FIGS. 2A and 2B are screenshots of a status section 200 of a conventional treatment display of a hemodialysis machine.

The status section 200 includes a status box 202 and a dialog box 204, which display notification information during an operation performed by the hemodialysis machine. The treatment display can also include a set of screen buttons and treatment parameters, for example, related to current venous pressure, pump rate, and dialysate conductivity levels. A user can control the operation of the hemodialysis machine from the treatment display by monitoring vital patient information such as blood pressure and temperature as well as machine-related information such as dialysate temperature and conductivity levels, and if appropriate, changing the treatment parameters.

When an abnormal event occurs, for example, a particular treatment parameter falls outside a predetermined range, or an operator enters an unacceptable parameter value, the status box 202 and/or the dialog box 204 can display a notification corresponding to the event. The event can be referred to as a current event, or a pending or active event. Such events can occur prior to or during a treatment, between treatments, during a test performed on the dialysis system 100, or in relation with another activity that includes the dialysis system 100. In an embodiment, notifications are generated in response to the detection of a current event. In the above-mentioned example, when a particular treatment parameter is determined to fall within a predetermined range, the notification corresponding to this current event can be removed from display, or removed from computer storage so that the notification cannot be displayed during cycling between current notifications. The notification can be removed automatically from the display or removed in response to an operator input, for example, a reset signal generated in response to an operator selecting a button or key at the control panel 134.

During normal operation, the status box 202 displays the operational mode of the machine, for example, a dialysis mode, indicating that a dialysis operation is in progress. However, when the dialysis operation is paused, a status advisory notification can be displayed at the status box 202, more specifically, a Dialysis Paused message.

The dialog box 204 can display additional information regarding an event. For example, when a user attempts to enter a treatment parameter that is outside an allowable range, the dialog box 204 can display an dialog message 214, for example, "Maximum UF rate reached . . . ," as shown in FIG. 2B. The dialog box 204 can display default information such as a set of current measurements, for example, a current time 206, a time of occurrence 208 of the most recent blood pressure reading, the patient's blood pressure reading 210 at the time of occurrence, and the patient's pulse rate 212 at the time of occurrence. However, only one alarm is displayed at a time in the status box 202, and only one dialog message is displayed at a time in the dialog box 204, which prevents a viewer from receiving a comprehensive operational status when multiple events occur.

FIG. 3A is a screenshot of a status section 300 of a treatment display, in accordance with an embodiment. In an embodiment, the status section 300 includes a status box 302, a dialog box 304, and a notification summary box 306. The status box 302 and the dialog box 304 perform operations that are similar to those of the status box 202 and dialog box 204 of the example of FIG. 2.

The notification summary box 306 in accordance with the present embodiment is positioned in a region between the status box 302 and the dialog box 304. Alternatively, the notification summary box 306 can be positioned at other regions relative to the status box 302 and dialog box 304, including at either side, and above and below the status box 302 and the dialog box 304. Alternatively, the notification summary box 306 can be positioned in other regions of the treatment display. In the present example embodiment, the notification summary box 306 comprises three notification buttons and three notification fields, each field corresponding to a button. The notification buttons include an alarm summary button 308, a warning summary button 312, and a dialog message summary button 316. An alarm field 310 is adjacent the alarm summary button 308, and displays a number corresponding to a set of alarm messages generated by the dialysis system 100. A warning field 314 is adjacent the warning summary button 312, and displays a number corresponding to a set of warning messages or status advisory messages generated by the dialysis system 100. A dialog message field 318 is adjacent the dialog message summary button 316, and displays a number corresponding to a set of dialog messages generated by the dialysis system 100. The notification buttons 308, 312, 316 can be selected by a mouse, keypad, keyboard, touch-sensitive screen, or other input/output device of the control panel 134. When the alarm summary button 308 is selected, the highest priority alarm message is displayed at the status box 302. When the warning summary button 312 is selected, the highest priority warning or status advisory message is displayed at the status box 302. When the dialog message summary button 316 is selected, the highest priority dialog message is displayed at the dialog box 304.

In FIG. 3A, the notification summary box 306 indicates that no alarms, warnings, status advisory messages, or dialog messages are generated. Accordingly, the status box 302 can display a status advisory notification indicating an operational mode, more specifically in the present example, a "Dialysis Paused" message. The dialog box 304 can display default information such as the current time, blood pressure readings, and the like.

Figure 3B:
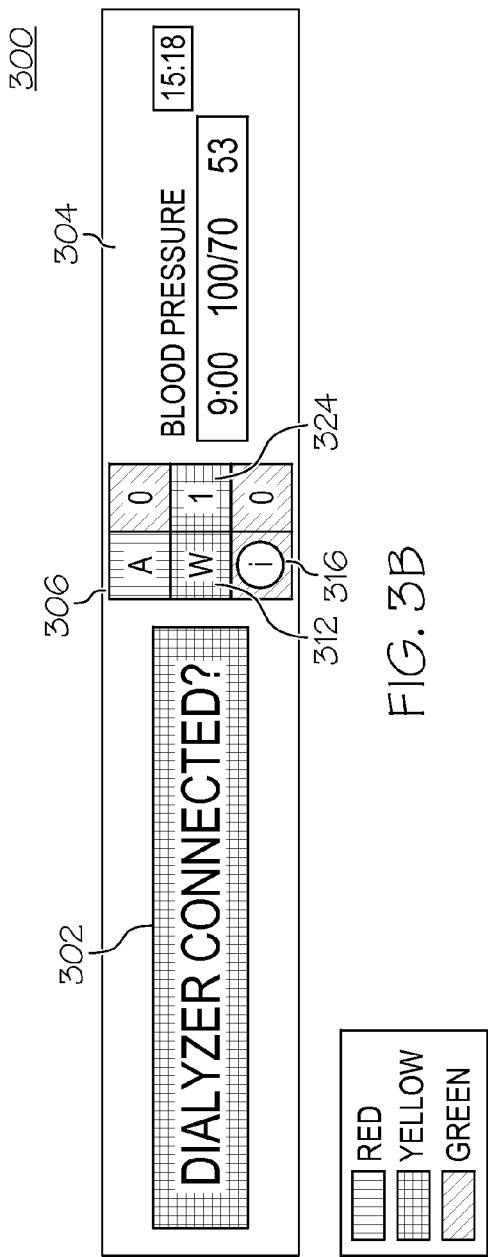
FIG. 3B is another screenshot of the status section of FIG. 3A, in accordance with an embodiment.

FIG. 3B is another screenshot of the status section 300 of FIG. 3A, in accordance with an embodiment. In this example, the notification summary box 306 includes a warning field 324 indicating that one warning message is generated. The warning message, i.e., a "Dialyzer Connected?" message is displayed at the status box 302. The status box 302, the warning field 324, and the corresponding warning summary button 312 can be displayed having a same color, for example, yellow. In this manner, a person viewing the status section 300 can be quickly informed of the type and severity of the event. Other indicators, for example, color codes, can be provided that correspond to other notification types of varying severities. For example, the alarm field 310 and corresponding alarm summary button 308 can be displayed as red when an alarm is generated and the dialog message field 318 and corresponding dialog message summary button 316 can be displayed in green. When an alarm is displayed for viewing by a user, the status box 302 can be displayed in red, when a warning is displayed, the status box 302 can be displayed in yellow, and when a status advisory message is displayed, the status box 302 can be displayed in green. Dialog box messages have no effect on the color of the status box 302 unless an operator action also triggers a warning or an alarm in response to an incorrect data entry.

Figure 3C:
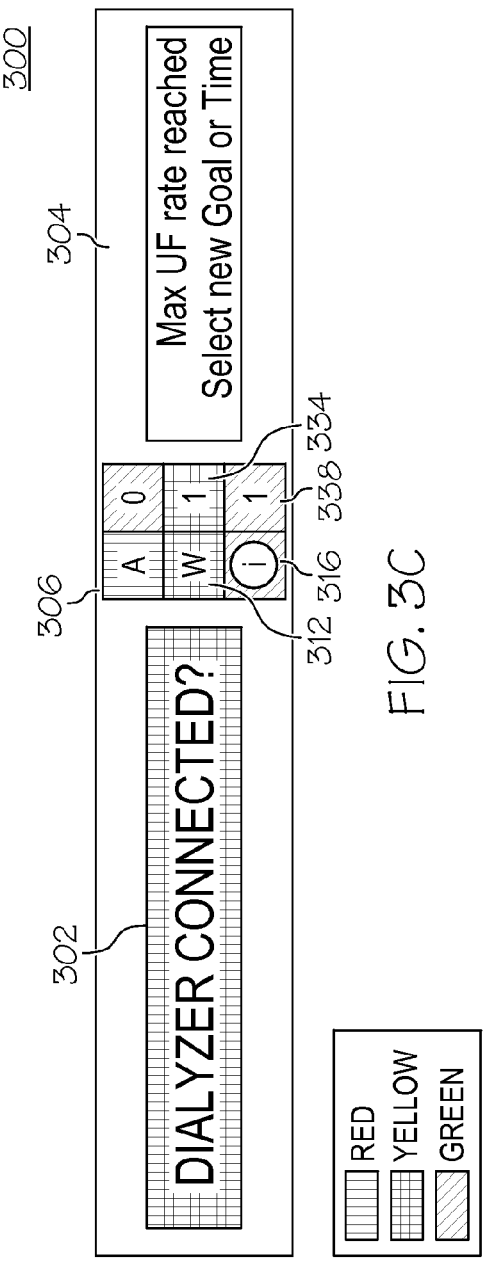
FIG. 3C is another screenshot of a status section of FIGS. 3A and 3B, in accordance with an embodiment.

FIG. 3C is another screenshot of the status section 300 of FIG. 3A, in accordance with an embodiment. In this example, the notification summary box 306 includes a warning field 334 indicating that one warning is generated, similar to the warning field 324 shown in FIG. 3B. The notification summary box 306 also includes a dialog message field 338 indicating that one dialog message is generated. A corresponding dialog message "Max UF rate reached . . . " is displayed at the dialog box 304.

When the event causing the warning to be generated is addressed and corrected, then the warning message "Dialyzer Connected?" is cleared from the status box 302 and replaced with a status advisory message, for example, Dialysis Paused, or replaced with another warning or alarm, depending on whether other events are present in the dialysis system 100. A user can clear an event caused by an incorrectly entered parameter and the like by reentering a correct parameter, for example, by entering a new goal or time in accordance with the dialog message in FIG. 3C. The dialog message "Max UF rate reached . . . " is cleared from the dialog box 304, and replaced with another pending dialog message or with default information such as a current set of readings as shown in FIGS. 3A and 3B.

FIG. 4 is a flowchart of a method 400 for displaying a notification in response to a dialysis event, in accordance with an embodiment. The event can be a regenerative dialysis event or a non-regenerative dialysis event. In describing the method 400, reference is made to the dialysis system of FIG. 1 and the status section 300 of FIGS. 3A-3C. Some or all of the method 400 can be implemented, for example, in the notification system 132 and/or the control panel 134 of FIG. 1.

In this example embodiment, the method 400 begins at step 402 with the detection of an event at the dialysis system 100. Events such as low blood pressure and the like can be detected by one or more monitors, meters, sensors, detectors, and the like as described in connection with FIG. 1. An event can be detected prior to a dialysis treatment, for example, when performing an alarm test or a pressure holding test (PHT), which can be performed to ensure pressure integrity of the dialysis machine's hydraulic system. Alternatively, an event can also be detected during operation, for example, during a dialysis treatment. An event can be caused by a malfunctioning element of the dialysis system 100, a change in status in the patient undergoing a dialysis treatment, a user error occurring when entering data to the control panel 134, or any abnormality subject to detection. In addition, events can optionally be generated in response to an element of the dialysis system 100 that is functioning properly, or to indicate a normally operating dialysis procedure.

A new notification is generated (step 404) in response to detection of the event. In accordance with the present example embodiment, the notification can be an alarm, a warning, or a status advisory message, depending on the nature and/or the severity of the event. The notification can be a dialog message that provides additional information of interest to a user, for example, a warning of an incorrectly entered parameter to the control panel 134.

The notification summary box 306 is updated (step 406) by changing a value, for example, by incrementing a value corresponding to a number of currently pending notifications. For example, in response to a newly generated warning, the number of pending warning messages can be increased from zero warning messages as shown in the warning field 314 of FIG. 3A to one warning message as shown in the warning field 324 of FIG. 3B. The corresponding notification field, e.g., warning field 324, can flash or provide another indicator that the new notification has been generated.

A determination is made (decision step 408) as to whether another notification is presently displayed at either the status box 302 or the dialog box 304 of the display screen. In the event that no other notification is displayed at the status box 302 or the dialog box 304, then the new notification is displayed (step 416). For example, if no other alarm, warning, or status advisory message is displayed at the status box 302, then a newly generated alarm, warning, or status advisory message can be displayed. Similarly, in the event that no other dialog message is displayed at the dialog box 304, or if default information is displayed, then a new dialog message can be displayed at the dialog box 304.

In the event that another notification is displayed at the status box or the dialog box, then a determination is made (decision step 410) as to whether the other notification has a higher priority than the new notification. The priority of each notification can be determined by a rules engine (not shown) that includes a set of rules establishing priorities between different alarms, warnings, status advisory messages, and dialog messages, or between a combination thereof. For example, when two alarm events related to a low dialysate conductivity and a high dialysate temperature, respectively, are detected, the rules engine establishes a priority for each event, for example, based on the severity of the event. In this example, the rules engine establishes that the low dialysate conductivity event has a higher priority than the high dialysate temperature, for example, because a low dialysate conductivity is deemed more dangerous to a patient than a high dialysate temperature.

In the event that a currently displayed notification has a higher priority than the new notification, then the new notification is stored (step 414), where it can be retrieved later for display. Otherwise, in the event that the new notification has a higher priority than the currently displayed notification, then the new notification is displayed (step 416). Other priority-based decision making approaches are equally applicable to the principles of the present inventive concepts. For example, a decision can be made that, under certain circumstances, lower priority notifications are to be displayed first.

FIG. 5 is a screenshot of a status section 500 of a treatment display presenting an alarm notification in accordance with the method of FIG. 4, in accordance with another embodiment. In this example, a notification summary box 506 includes an alarm summary button 508 and a corresponding alarm field 510 indicating that one alarm is generated, a warning summary button and a corresponding warning field 514 indicating that one warning is generated, and a dialog summary button 516 and a corresponding dialog message field 518 indicating that one dialog message is generated. The notification system 132 determines that a "Conductivity Low" alarm-related event has a higher priority than the warning-related event (not shown). Therefore, in accordance with the method 400, the alarm message, i.e., "Conductivity Low", is displayed at the status box 502. In an embodiment, the status box 502 and the alarm field 510 display a same color, i.e., red, permitting a viewer to quickly determine a number of current alarms as well as the displayed alarm message.

Selecting any of the three buttons 508, 512, 516 will cause the highest priority notification of the number of notifications displayed at a corresponding field 510, 514, 518, respectively, to be displayed. In FIG. 5, the alarm summary button 508 is displayed because it is the highest priority alarm, warning, or status advisory message. In FIG. 5, only one alarm is shown in the alarm field 510, so the alarm message "Conductivity Low" is displayed.

Figure 6:
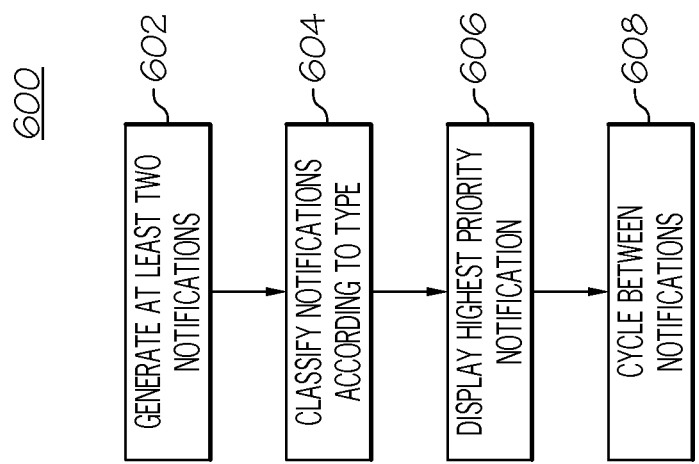
FIG. 6 is a flowchart of a method for selecting a notification for display, in accordance with an embodiment.

FIG. 6 is a flowchart of a method 600 for selecting a notification for display, in accordance with an embodiment. In describing the method 600, reference is also made to the dialysis system of FIG. 1 and the status section 300 of FIGS. 3A-3C. Some or all of the method 600 can be implemented, for example, in the notification system 132 and/or the control panel 134 described in FIG. 1.

In this example embodiment, the method 600 begins at step 602 where at least two notifications are generated. The notifications can be alarms, warnings, status advisory messages, dialog messages, or a combination thereof.

The notifications are classified (step 604) according to a type of notification. For example, all pending notifications can be classified as alarms, warnings/status advisory messages, or dialog messages. A total number of pending alarms is determined, and displayed at the alarm field 308 of the notification summary box 306. Similarly, a total number of pending warnings and/or advisory messages is determined, and displayed at the warning field 314, 324, 334 of the notification summary box 306. A total number of dialog messages is displayed at the dialog message field 318, 338 of the notification summary box 306.

The highest priority notification among the generated notifications is displayed (step 606), for example, according to the method 400 described above in connection with FIG. 4. In the present example embodiment, alarms have a higher priority than warnings, and warnings have a higher priority than status advisory messages.

A user can cycle (step 608) between notifications. For example, a user can press the [Confirm] key or [Up] arrow key on a keyboard connected to the control panel 134 to cycle through all current alarms, warnings, and/or status advisory messages stored in the notification system 132 such that each stored alarm, warning, and/or status advisory message is displayed, one at a time, in the status box 302. Similarly, a user can cycle through all current dialog box messages such that each dialog message is displayed, one at a time, in the dialog box 304.

In an embodiment, the notifications are cycled according to a predetermined priority of each notification. For example, as described above with regard to step 606, the highest priority notification is displayed first. The next highest priority notification can be displayed when the user performs the cycling step 608, and so on until the lowest priority notification is displayed. During operation, a user can select the alarm summary button 308 at the notification summary box 308 to display the highest priority alarm cycle through all current alarms. After all of the current alarms are displayed, the next applicable field, for example, the warning field 314, can be automatically activated, where the warnings and advisory messages can be displayed, one at a time, according to priority. Alternatively, cycling can occur within a particular category, for example, an alarm category. Here, a user can select a different field, for example, the warning field 314, and use a mouse, keyboard keys, and the like, to cycle between warnings and status advisory messages. Thus, the cycling step can include automatic or manual cycling of the notifications, with each notification being displayed by the notification system 132 or control panel 134 for a certain period of time, for review by a user. After cycling through the notifications, the cycling step can be restarted at the highest priority notification, or the cycling step can terminate at the lowest priority notification, for example, if two or more control panel keys or buttons are used such as an up key to display a higher priority notification and a down key to display a lower priority notifications.

Figure 7A:
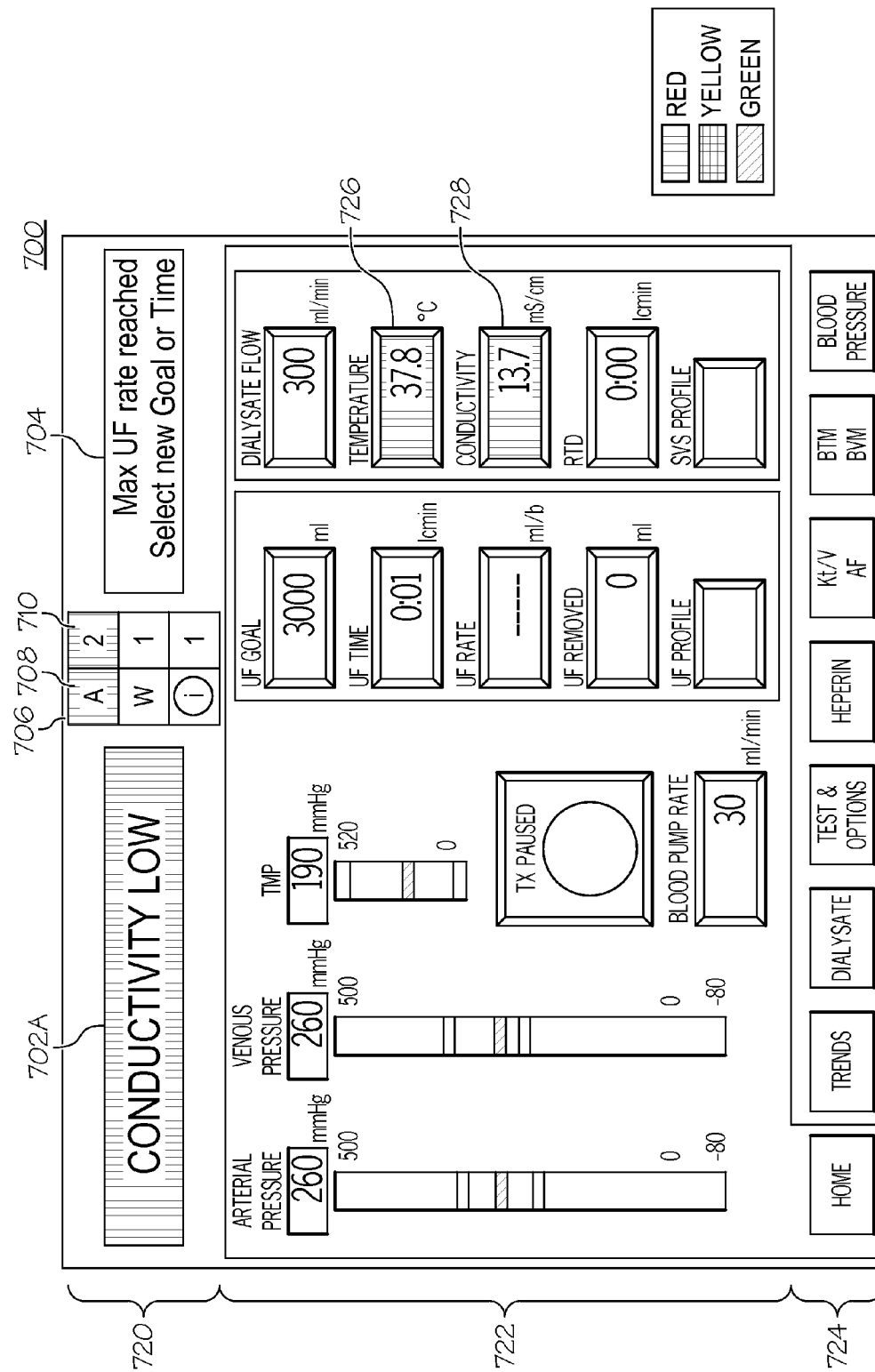
FIGS. 7A and 7B are screenshots of a treatment display presenting notifications complying with the method of FIG. 6, in accordance with an embodiment.
Figure 7B:
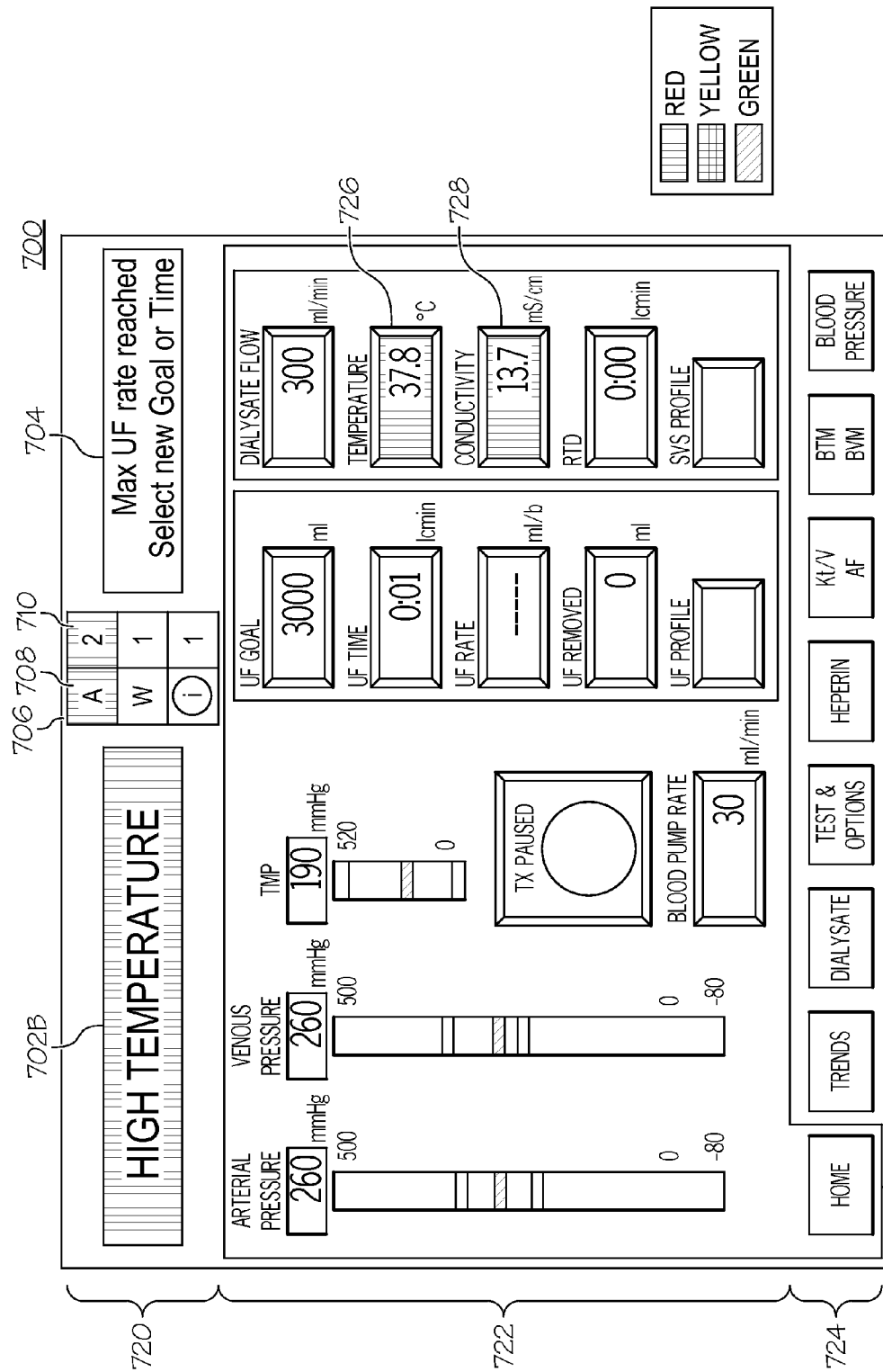

FIGS. 7A and 7B are screenshots of a treatment display 700 presenting notifications in accordance with the method of FIG. 6, in accordance with an embodiment.

The treatment display 700 comprises a status section 720, a treatment display window 722, and a set of screen buttons 724, also referred to as treatment display keys. The status section 720 is similar to the status sections described herein.

The treatment display window 722 includes a region for viewing various treatment data, such as UF data, arterial, venous, and transmembrane pressures, and dialysate data. An operator can set treatment parameters and monitor the treatment at the treatment display window 722.

The screen buttons 724 are used to access and view the various treatment screens displayed at the treatment display window 722. For example, as shown in FIGS. 7A and 7B, a home screen button 732 can be selected for displaying the various treatment data, e.g., UF data and the like.

An alarm field 710 of the notification summary box 706 indicates that two alarms are generated. In this example, the first alarm is a low conductivity alarm. The actual current conductivity (13.7 mS/cm) is displayed at a conductivity field 728 of the treatment display window 722. The second alarm is a high temperature alarm. The actual current temperature (37.8° C.) is displayed at a temperature field 726 of the treatment display window 722. Each alarm has a predetermined priority. The higher priority alarm, i.e., "Conductivity Low," is displayed at the status box 702 as shown in FIG. 7A. The lower priority alarm, i.e., "High Temperature," is displayed at the status box 702 as shown in FIG. 7B when a user cycles between the two alarms in accordance with the method 600. The conductivity field 728 and the temperature field 726 can display a same color as the status box 702, the alarm button 708, and corresponding alarm field 710 for easy identification by a viewer.

FIGS. 8A-8C are screenshots of a status section 800 of a treatment display presenting a time of occurrence of past and present alarms, in accordance with another embodiment.

An operator can select a key, for example, a down arrow key at the control panel 134, to display a time of occurrence of an event in the notification summary box 804. The time of occurrence can be displayed at a region of the notification summary box 804 corresponding to the type of displayed notification. In particular, as shown in FIG. 8A, a Conductivity Low alarm notification is displayed at the status box 802. The current time is 15:18 (24 hour format) as shown in the dialog box 804. When an operator selects a down arrow or other key at the control panel 134, the time of occurrence (15:15) of the event, i.e., the Conductivity Low event, is displayed at the notification summary box 806, more specifically, displayed at an alarm region 808 of the notification summary box 806. The previously displayed alarm button and corresponding alarm field are replaced with the time of occurrence. However, the number of outstanding warnings and/or status advisory messages and dialog messages continues to be displayed at the notification summary box 804.

In FIG. 8B, a Dialyzer Connected warning message is displayed at the status box 802. A time of occurrence (15:15) of the event generating this notification can be displayed at the warning region 812 of the notification summary box 806. The previously displayed warning button and corresponding warning field are replaced in the notification summary box 806 with the time of occurrence. However, the number of outstanding alarms and dialog messages continues to be displayed at the notification summary box 806.

In FIG. 8C, a dialog message is displayed at the dialog box 804 indicating that a user attempted to change the UF rate to an unacceptable value. A time of occurrence (15:18) of this current event can be displayed at the dialog message region 816 of the notification summary box 806. The previously displayed dialog message button and corresponding dialog message field are replaced with the time of occurrence. However, the number of outstanding alarms and warnings continues to be displayed at the notification summary box 806.

In an embodiment, the status box 802 is displayed having the color corresponding of the highest priority alarm currently present, even when an operator views previous notifications. For example, referring to FIGS. 8A-8C, the status box 802 can display a border or filling having a color corresponding to the highest priority alarm when an operator views previous messages in the status box 802 and/or dialog box 804. For example, in FIG. 8A, a previous event, i.e., a Conductivity Low event, having a time of occurrence (15:15) can be displayed in the status box 802. However, when there are no current alarms or warnings, the status box 802 is displayed in green. In another example, a previous warning can be displayed in the status box 802 even when a high priority alarm, for example, a high temperature alarm, is generated. Here, the status box 802 is displayed in red, even if an operator is viewing a previous warning at the status box 802. Therefore, in this embodiment, the color of the status box 802 is always predicated on the highest priority alarm, warning, or advisory message currently present. Accordingly, the operator can view messages corresponding to previous notifications with a reduced likelihood of mistakingly believing that an outstanding alarm or warning has been resolved.

Figure 9:
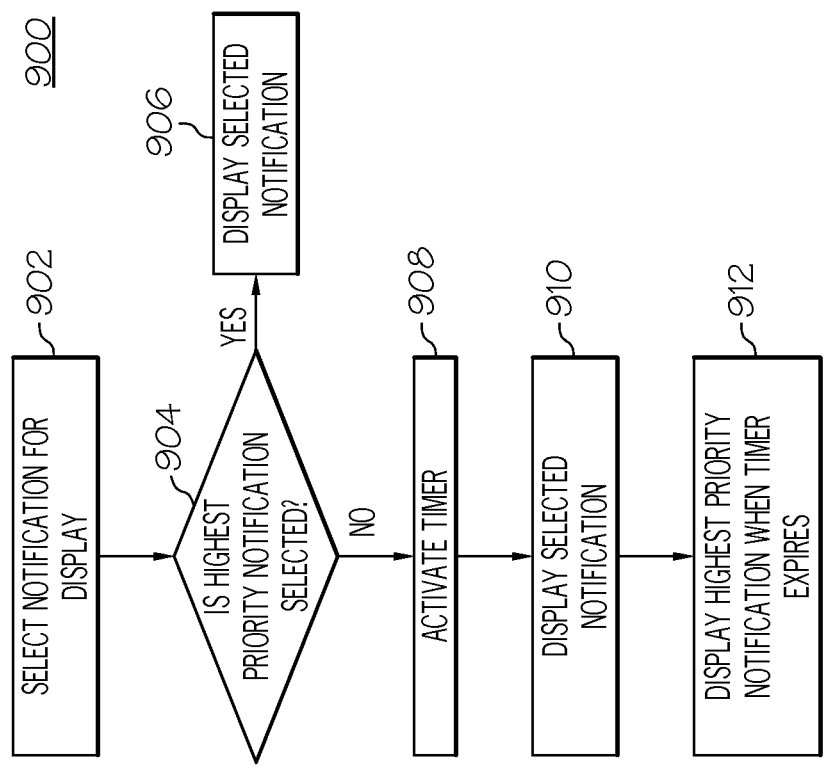
FIG. 9 is a flowchart of a method for displaying a notification having a highest priority, in accordance with an embodiment.

FIG. 9 is a flowchart of a method 900 for displaying a notification having a highest priority, in accordance with an embodiment. In describing the method 900, reference is also made to the dialysis system of FIG. 1 and the status section 300 of FIGS. 3A-3C. Some or all of the method 900 can be implemented, for example, in the notification system 132 and/or the control panel 134 described in FIG. 1.

An operator selects (step 902) a type of notification for display. The operator can select a button in the notification summary box, for example, an alarm button 308 shown in FIG. 3, to display one alarm at a time in the status box 302.

The notification system 132 is configured to display by default the highest priority alarm, warning, or status advisory message in the status box 302, or the highest priority dialog message is displayed at the dialog box 304. The operator can select different notifications for display as described herein, for example, by cycling between different alarms. Thus, a determination is made (step 904) whether a selected notification is the highest priority notification of a set of current notifications.

If the selected notification is the highest priority notification, then the selected notification is displayed (step 906) in the status box 302 if the selected notification is a highest priority alarm, warning, or status advisory message, or displayed at the dialog box 304 if the selected notification is a highest priority dialog message.

If the selected notification is a lower priority notification, then a timer is activated (step 908) according to a predefined time, which can be user-defined or hardcoded, and the selected lower priority notification is displayed (step 910) in the status box 302 or the dialog box 304, depending on the type of notification. The highest priority notification is displayed (step 912) in the status box 302 or the dialog box 304, depending on the type of notification, when the timer expires. Alternatively, a user can select an escape key and the like and return the highest priority notification to the appropriate display before the timer expires.

Figure 10A:
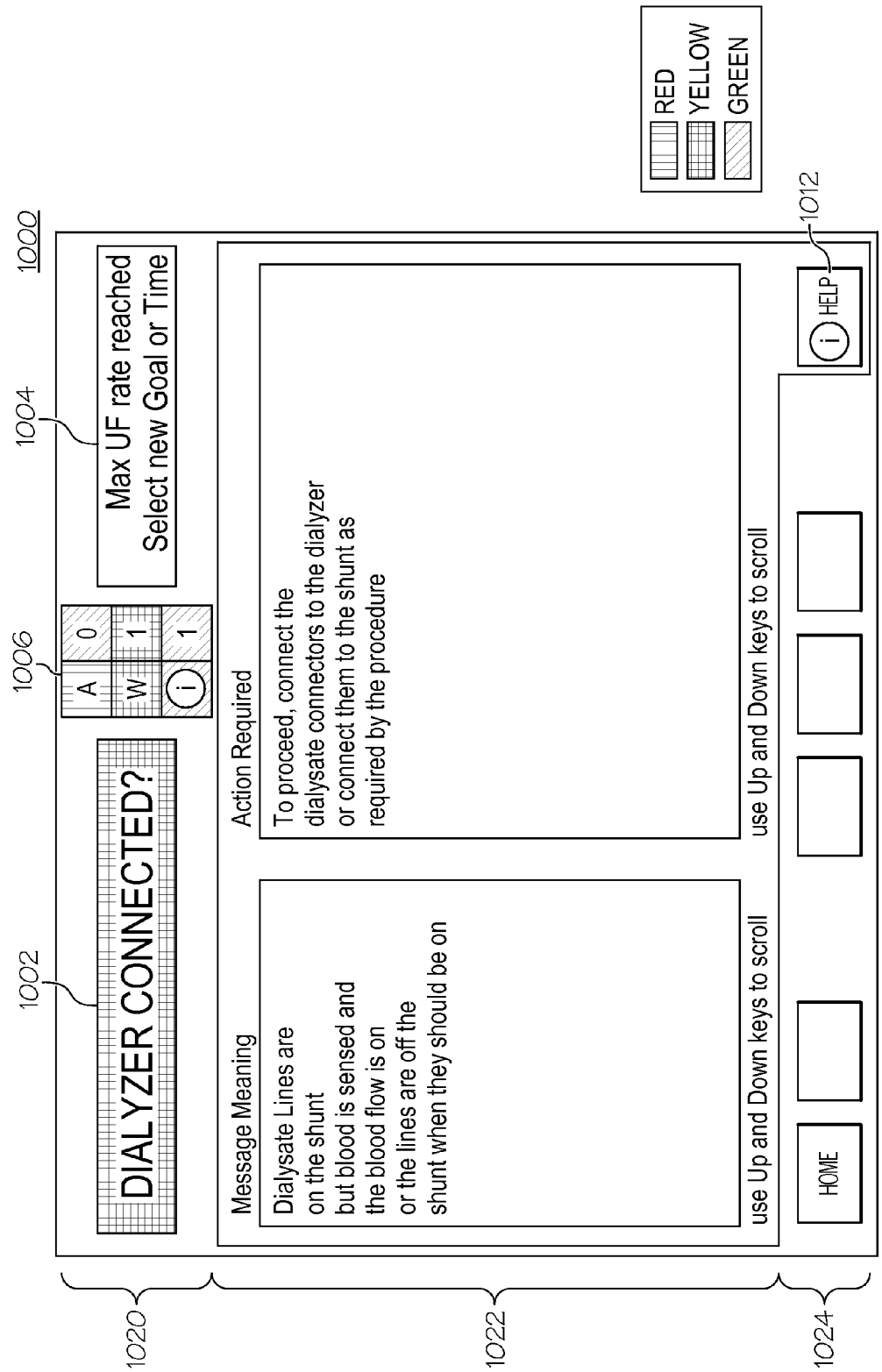
FIG. 10A is a screenshot of a help screen message displayed on a control panel, in accordance with an embodiment.

FIG. 10A is a screenshot of a help screen message displayed at a treatment display 1000, in accordance with an embodiment. The treatment display 1000 comprises a status section 1020, a help screen 1022, and a set of screen buttons 1024, including a Help key 1012.

The help screen 1022 corresponds to a displayed notification in a status box 1002 of the status section 1020. If more than one notification is generated, a help screen message can be provided for each notification. A user can first press the Help key 1012 on the control panel, then press a [Confirm] key or an [Up] arrow key from a keyboard to cycle through and display the help screen messages. For example, a user can cycle to the next help screen message, which displays help information (not shown) regarding the dialog message "Max UF rate reached . . . " displayed at the dialog box 1004 of the status section 1020. In order to display the help information for the dialog box message, the user can select the dialog field. Alternatively, the dialog field is automatically selected for cycling through the help screen messages for all pending alarms, warnings, advisory messages, and/or dialog box messages.

Figure 10B:
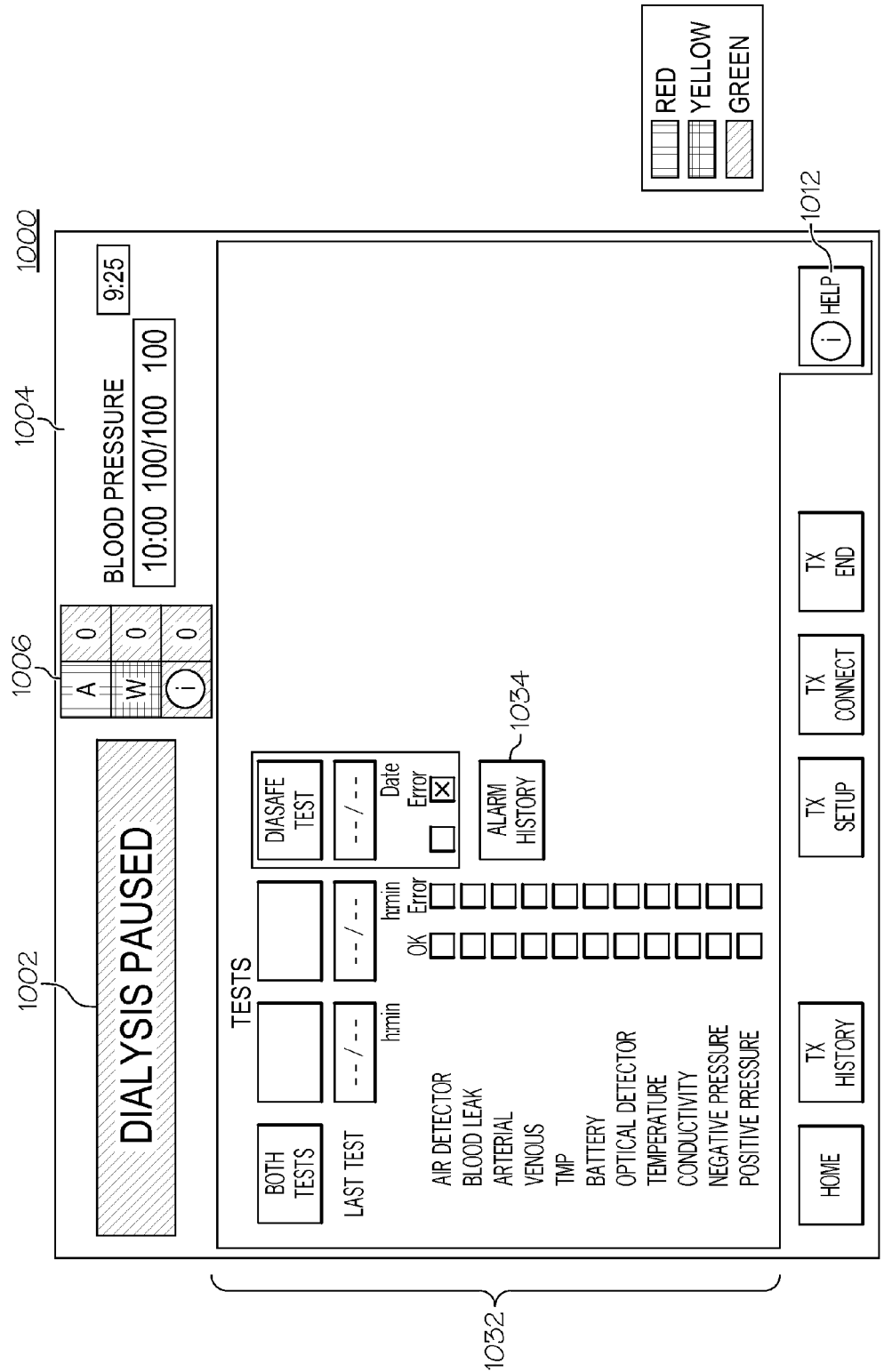
FIG. 10B is a screenshot of a default screen displayed on a control panel when no alarms, warnings, or dialog messages are present, in accordance with an embodiment.

FIG. 10B illustrates a default help screen 1032 displayed when no notifications are generated, as shown in the notification summary box 1006. The default help screen 1032 can be a test and options screen that permits an operator to perform tests on the hemodialysis machine 104 to ensure that it is functioning properly. The default help screen 1032 can include an alarm history button 1034 to allow the user to cycle through previous alarms when no alarm is currently present. Thus, a user can scroll previously generated alarms or other notifications to view a time of occurrence and other help screen information related to the previously generated notifications. A default configuration can be provided where the most recent notification and its corresponding help screen information can be displayed when the alarm history button is selected. An alarm summary button, a warning summary button, or a dialog message summary button of the notification summary box 1006 can be selected for cycling, i.e., manually or automatically, via previous notifications corresponding to the selected button as well as corresponding help screen information, time of occurrence, and the like.

Figure 10C:
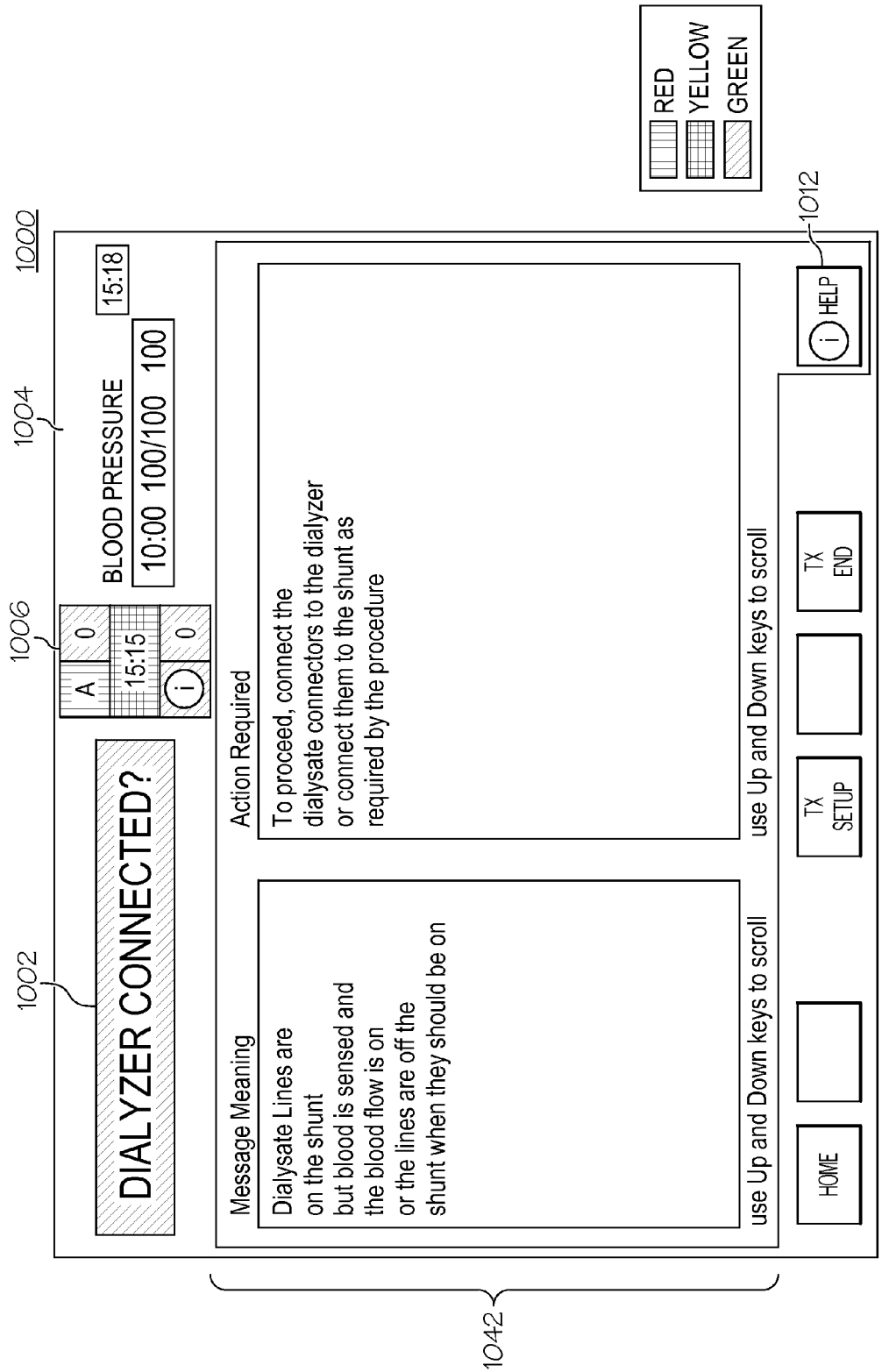
FIG. 10C is a screenshot of a help screen message corresponding to a previously generated notification, in accordance with an embodiment.

FIG. 10C illustrates a stored help screen message 1042 corresponding to a previously generated warning. As shown in the notification summary box 1006, a warning was generated at 15:15. The help screen message 1042 is generated for this warning, and is displayed by the user by selecting the warning summary button or the alarm history button if it is the most recent notification.

Figure 11:
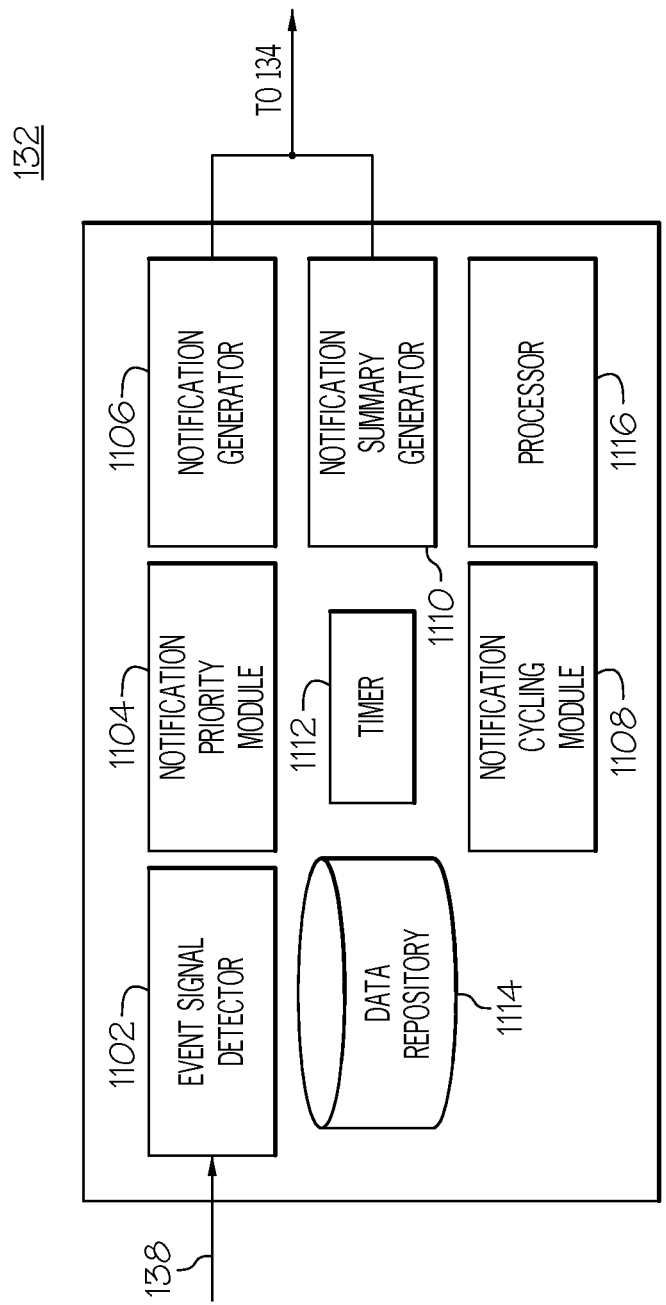
FIG. 11 is a block diagram of the notification system of FIG. 1, in accordance with an embodiment.

FIG. 11 is a block diagram of the notification system 132 of FIG. 1, in accordance with an embodiment. The notification system 132 includes a plurality of computation units that can be implemented in any of a number of different configurations, depending on the desired architecture. For example, the computation units can comprise software modules that operate on, or in connection with, one or more processors, and/or other firmware or hardware.

The notification system 132 in accordance with the present embodiment comprises an event signal detector 1102, a notification priority module 1104, a notification generator 1106, a notification cycling module 1108, a notification summary generator 1110, a timer 1112, a data repository 1114, and a processor 1116, which can communicate with each other via a bus and/or data connector, for example, a peripheral component interconnect (PCI) bus.

The event signal detector 1102 receives an event signal 138 from a monitor, meter, sensor, or related device of the dialysis system 100, for example, a venous pressure monitor 130. The event signal 138 includes information related to the type of event. For example, an event signal 138 generated from the dialysate conductivity monitor 108 can indicate a low dialysate conductivity. The event signal 138 can be an analog or a digital signal, or other electrical signal.

The notification priority module 1104 generates a prioritized notification signal from each received event signal 138. Priorities are determined by a rules engine (not shown) that provides a set of rules establishing priorities between different alarms, warnings, status advisory messages, dialog messages, or between a combination thereof. For example, when alarm events related to a low dialysate conductivity and a high dialysate temperature, respectively, are detected, the notification priority module 1104 refers to the rules engine to determine the priority of each event, for example, based on the severity of the event. In this example, the rules engine establishes that the low dialysate conductivity event has a higher priority than the high dialysate temperature, for example, because a low dialysate conductivity is deemed more dangerous to a patient than a high dialysate temperature.

The notification generator 1106 outputs notifications such as alarms, warnings, status advisory messages, and/or dialog box messages to the control panel 134 for display based on priority, type of notification, and the like from the prioritized notification signals.

The notification summary generator 1110 includes a counter (not shown) that tracks a number of outstanding notifications according to a notification type. The notification summary generator 1110 generates a current value for each type, i.e., a number of outstanding alarms, warnings, and dialog box messages, and outputs the number from the counter to the control panel 134. The current values can be output to, and displayed from, a field of the notification summary box 306, i.e, field 310, 314, or 318. The notification summary generator 1110 can increment the total number of alarms, warnings, etc. when a new notification such as an alarm, warning, status advisory message, or dialog box message is detected. The notification summary generator 1110 can alternatively decrement the displayed number of alarms, warnings, etc. when a corresponding event is addressed. For example, referring to FIG. 7A, when a conductivity level is increased to an acceptable level, the corresponding Conductivity Alarm is cleared, for example, removed from the data repository 1114, and the number of alarms in the alarm field 710 of the notification summary box 706 is reduced accordingly.

The notification summary generator 1110 permits a user to display different alarms, warnings, status advisory messages, and/or dialog messages by selecting an appropriate button. For example, when the alarm button 308 is selected, a user can cycle between different alarm messages which are displayed at the status box 302. A user can alternatively display other information such as the time of occurrence of present and past alarms, selecting help screen messages, and the like as described herein.

The notification cycling module 1108 enables a user to display different current notifications other than the highest priority notification. In particular, the notification cycling module 1108 can retrieve notification data from the data repository 1114 for display. During operation, a user can cycle between different notifications as well as between help screens corresponding to these notifications, whereby the notification cycling module 1108 retrieves the notifications according to priority, chronological order, or other predetermined order. Automated cycling of the display of notifications can also be controlled by the notification cycling module 1108.

The timer 1112 tracks an amount of time that a current notification is displayed to ensure that the highest priority alarm is redisplayed at the status box 302 when the user selects for display a different alarm, warning, status advisory message, or dialog message. For example, if a low priority alarm is selected and displayed, the timer 1112 is activated to generate a timeout signal at the end of a predetermined period of time that replaces the displayed low priority alarm with the highest priority alarm generated among the current notifications. The timer 1112 can also be employed for other timing-related tasks.

The data repository 1114 stores historical and current notification data, for example, alarm history information. This information can include alarm, warning, status advisory, or dialog-related data for display at the notification summary box 306. Help details are also stored in the data repository. The data repository 1114 can include volatile memory, for example, RAM and the like, and/or non-volatile memory, for example, ROM, flash memory, and the like. The memory can include removable and/or non-removable storage media implemented in accordance with methods and technologies known to those of ordinary skill in the art for storing data. Stored in the memory can include program code, such as program code of an operating system, applications, or other modules described herein that can be executed by the processor 1116.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "module" or "system." For example, a module may be implemented as a hardware circuit comprising custom circuits, gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Furthermore, aspects of the present invention may take the form of a computer program product embodied in one or more computer readable medium(s) having computer readable program code embodied thereon. A storage device can include a computer readable storage medium, which may be, for example, but not limited to, an electronic, magnetic, optical, electromagnetic, infrared, or semiconductor system, apparatus, or device, or any suitable combination of the foregoing. Any combination of one or more computer readable medium(s) may be utilized. The computer readable medium may be a computer readable signal medium or a computer readable storage medium. Examples of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While embodiments of the invention has been shown and described, it should be understood by those skilled in the art that various changes in form and detail may be made therein without departing from the spirit and scope of the invention.

What is claimed is:

1. A computer-implemented method of performing dialysis and displaying information
in response to at least one event related to a treatment performed by a dialysis system, comprising:
providing a dialysis system comprising a dialysis machine and an extracorporeal circuit for removing blood from a patient, at least one of filtering and dialyzing of the blood, and returning cleaned blood to the patient, while monitoring safety-critical parameters within the circuit;
displaying a first number at a treatment display, the first number corresponding to a number of current notifications including messages corresponding to different events detected by the monitoring in an event category, the first number generated in response to at least one current event of the different events in the event category related to the treatment;
detecting a new event from the monitoring of the different events in the event category related to the treatment;
displaying a second number in response to detecting the new event, the second number corresponding to a combination of a new notification message generated in response to the new event in the event category and the message corresponding to the at least one current event of the different events in the event category number of current notifications;

determining a highest priority event between the new event and the at least one current event; and displaying at the treatment display at least one notification corresponding to the highest priority event enabling suggesting a course of action that corrects an abnormal monitored parameter.

2. The computer-implemented method of claim 1, further comprising:

configuring the treatment display to include a status box, a dialog box, and a notification summary box;

displaying at least one of the first number and the second number at the notification summary box; and displaying the at least one notification corresponding to the highest priority event at the status box or the dialog box.

3. The computer-implemented method of claim 2, wherein the at least one of the first number and the second number is displayed at a first region of the notification summary box corresponding to a set of alarm notifications, or is displayed at a second region of the notification summary box corresponding to a set of advisory notifications, or is displayed at a third region of the notification summary box corresponding to a set of dialog messages.

4. The computer-implemented method of claim 3, wherein the set of advisory notifications include at least one of a warning message and a status advisory message.

5. The computer-implemented method of claim 3, further comprising:

displaying an alarm notification, warning notification, or a status advisory notification of the set of alarm notifications and the advisory notifications, respectively, at the status box of the treatment display.

6. The computer-implemented method of claim 3, further comprising:

displaying a dialog message of the set of dialog messages at the dialog box of the treatment display.

7. The computer-implemented method of claim 2, further comprising displaying at the notification summary box a time of occurrence of the highest priority event.

8. The computer-implemented method of claim 1, further comprising:

cycling between the at least one notification corresponding to the highest priority event and the current notifications corresponding to lower priority events; and displaying at the treatment display a current notification of the number of current notifications during the cycling.

9. The computer-implemented method of claim 8, further comprising displaying a help screen at the treatment display corresponding to the displayed current notification of the number of current notifications or the displayed at least one notification corresponding to the highest priority event.

10. The computer-implemented method of claim 8, further comprising:

displaying at the notification summary box a time of occurrence of an event of the at least one current event from which the displayed current notification of the number of current notifications is generated.

11. The computer-implemented method of claim 8, further comprising:

storing the number of current notifications and the at least one notification corresponding to the highest priority event at a storage device; and retrieving the stored current notification of the current notifications for display during the cycling between the at least one notification corresponding to the highest priority event and the current notifications.

12. The computer-implemented method of claim 8, wherein the highest priority event complies with a color code, each color in the color code referring to a severity of the event, and wherein the current notification is displayed during the cycling at a region of the treatment display that displays a color of the color code corresponding to the highest priority event.

13. The computer-implemented method of claim 1, further comprising:

displaying a first notification corresponding to the highest priority event;

selecting for display a second notification corresponding to a lower priority event between the new event and the at least one current event;

configuring a timer to display the second notification for a predefined period of time;

displaying the second notification during the predefined period of time; and automatically displaying the first notification following the predefined period of time.

14. The computer-implemented method of claim 1, wherein the first number is zero, and wherein a default status advisory message is displayed at the treatment display.

15. The computer-implemented method of claim 1, wherein determining a highest priority event includes determining a highest priority between different alarms, warnings, status advisory messages, dialog messages, or a combination thereof.

16. The computer-implemented method of claim 1, wherein the at least one current event is an incorrectly entered parameter for configuring the dialysis system or an event capable of endangering a patient during a dialysis procedure.

17. The computer-implemented method of claim 1, further comprising displaying a time of occurrence of each message.

18. A notification system comprised in a dialysis system, the dialysis system comprising a dialysis system comprising a dialysis machine and an extracorporeal circuit for removing blood from a patient, at least one of filtering and dialyzing of the blood, and returning cleaned blood to the patient, and including a device for monitoring safety-critical parameters within the circuit:

an event signal detector that receives event signals generated in response to detected events of different events in an event category related to a treatment performed by the dialysis system and detected by the device for monitoring;

a notification generator that processes the event signals to generate a number of notifications including messages corresponding to the different events in the event category;

a notification summary generator that generates a number corresponding to the number of notifications including messages corresponding to the different events in the event category; and further comprising a notification priority module that determines a priority of each event of the plurality of events in order to output a notification to the treatment display that corresponds to a highest priority event of the plurality of events and enabling suggesting a course of action that corrects an abnormal monitored parameter.

19. The notification system of claim 18, wherein the notification summary generator generates a first number corresponding to zero or more current notifications of the number of current notifications, and generates a second number in response to a detected new event, the second number corresponding to a combination of a new notification generated from the new event and the number of current notifications.

20. The notification system of claim 19, wherein the notification summary generator forms a notification summary box that is displayed at the treatment display and that is populated with at least one of the first number and the second number.

21. The notification system of claim 20, wherein the notification summary generator provides the at least one of the first number and the second number at a first region of the notification summary box corresponding to a set of alarm notifications, or at a second region of the notification summary box corresponding to a set of advisory notifications, or at a third region of the notification summary box corresponding to a set of dialog messages.

22. The notification system of claim 21, wherein the notification generator outputs to the notification summary box a time of occurrence of an event to which a currently displayed notification corresponds.

23. The computer-implemented method of claim 22, wherein the set of advisory notifications includes at least one of a warning message and a status advisory message.

24. The notification system of claim 18, further comprising:
    a timer that establishes a period of time during which a different notification than the notification corresponding to the highest priority event is displayed at the treatment display, and the timer automatically displays the notification corresponding to the highest priority event at the treatment display at the end of the period of time.

25. The notification system of claim 18, wherein the notification priority module determines a highest priority between different alarms, warnings, status advisory messages, dialog messages, or a combination thereof.

26. The notification system of claim 18, further comprising a notification cycling module and a data repository, the data repository storing the number of notifications, the notification cycling module retrieving a notification of the stored number of notifications for display during a cycling between the number of notifications.

27. The notification system of claim 26, wherein the notification cycling module retrieves help screen data corresponding to the number of notifications from the data repository and outputs the help screen data to the treatment display.

28. The notification system of claim 18, wherein the notification system displays a time of occurrence of each message.

29. A computer-implemented method of performing dialysis and determining a notification for display, the notification corresponding to an event related to a treatment performed by a dialysis system, the method comprising:
    providing a dialysis system comprising a dialysis machine and an extracorporeal circuit for removing blood from a patient, at least one of filtering and dialyzing of the blood, and returning cleaned blood to the patient, while monitoring safety-critical parameters within the circuit;
    generating at least two notifications, each notification generated in response to an event related to the treatment and including messages corresponding to different events detected by the monitoring in an event category;
    displaying at least one number corresponding to a number of the at least two notifications at a first region of a treatment display;
    displaying a first highest priority notification of the at least two notifications at a second region of the treatment display enabling suggesting a course of action that corrects an abnormal monitored parameter; and
    cycling between the first highest priority notification and other notifications of the at least two notifications to display at least one other notification of the other notifications at the treatment display.

30. The computer-implemented method of claim 29, wherein cycling between the first highest priority notification and other notifications includes:
    cycling between at least two alarms, warnings, status advisory messages, or a combination thereof; and
    displaying the at least two alarms, warnings, status advisory messages, or a combination thereof, one at a time, at a status box of the treatment display.

31. The computer-implemented method of claim 30, further comprising:
    cycling between the at least two alarms; and
    automatically activating a warning field at the first region of the treatment display to display one or more warnings, status advisory messages, or a combination thereof, at the status box.

32. The computer-implemented method of claim 31, further comprising:
    cycling between at least two warnings, status advisory messages, or a combination thereof, at the status box.

33. The computer-implemented method of claim 30, further comprising:
    cycling between the at least two alarms; and
    manually selecting a warning field at the first region of the treatment display to display one or more warnings, status advisory messages, or a combination thereof, at the status box.

34. The computer-implemented method of claim 33, further comprising:
    cycling between at least two warnings, status advisory messages, or a combination thereof, at the status box.

35. The computer-implemented method of claim 29, wherein cycling between the first highest priority notification and other notifications includes:
    cycling between at least two dialog messages; and
    displaying the at least two dialog messages, one at a time, at a dialog box of the treatment display.

36. The computer-implemented method of claim 29, wherein displaying the at least one number comprises:
    displaying a first number at the treatment display, the first number corresponding to the at least two notifications;
    detecting a new event related to the treatment;
    replacing the first number with a second number in response to detecting the new event, the second number corresponding to a combination of a new notification generated in response to the new event and the at least two notifications;
    determining a second highest priority notification between the new notification and the first highest priority notification; and
    displaying at the treatment display the second highest priority notification.

37. The computer-implemented method of claim 36, further comprising providing a notification summary box at the first region of the treatment display, wherein the at least one of the first number and the second number is displayed at a first section of the notification summary box corresponding to a set of alarm notifications, or is displayed at a second section of the notification summary box corresponding to a set of advisory notifications, or is displayed at a third section of the notification summary box corresponding to a set of dialog messages.

38. The computer-implemented method of claim 37, wherein the notification generator outputs to the notification summary box a time of occurrence of an event to which a currently displayed notification corresponds.

39. The computer-implemented method of claim 37, wherein the set of advisory notifications include at least one of a warning message and a status advisory message.

40. The computer-implemented method of claim 29, further comprising displaying a help screen at the treatment display corresponding to the displayed first highest priority notification.

41. The computer-implemented method of claim 29, further comprising displaying a help screen at the treatment display corresponding to the at least one other notification.

42. The computer-implemented method of claim 29, wherein displaying at least one other notification of the other notifications at the treatment display includes displaying each of the at least two notifications in an order of a predetermined priority of each notification.

43. The computer-implemented method of claim 29, wherein the first highest priority event complies with a color code, each color in the color code referring to a severity of the event, and wherein the other notification is displayed during the cycling at a region of the treatment display that displays a color of the color code corresponding to the first highest priority event.

44. The computer-implemented method of claim 29, further comprising displaying a time of occurrence of each message.

* * * * *